US008670822B2

(12) United States Patent
Karo et al.

(10) Patent No.: US 8,670,822 B2
(45) Date of Patent: Mar. 11, 2014

(54) BODY FAT MEASUREMENT DEVICE

(71) Applicant: Omron Healthcare Co., Ltd., Muko (JP)

(72) Inventors: Hiromichi Karo, Kyoto (JP); Takehiro Hamaguchi, Kyoto (JP); Kazuhisa Tanabe, Kyoto (JP); Yasuaki Murakawa, Kyoto (JP)

(73) Assignee: Omron Healthcare Co., Ltd., Muko-shi (JP)

( * ) Notice: Subject to any disclaimer, the term of this patent is extended or adjusted under 35 U.S.C. 154(b) by 0 days.

(21) Appl. No.: 13/749,412

(22) Filed: Jan. 24, 2013

(65) Prior Publication Data
US 2013/0137942 A1 May 30, 2013

Related U.S. Application Data

(63) Continuation of application No. PCT/JP2011/064285, filed on Jun. 22, 2011.

(30) Foreign Application Priority Data

Aug. 17, 2010 (JP) .................................. 2010-182359

(51) Int. Cl.
*A61B 5/00* (2006.01)
(52) U.S. Cl.
USPC .......................................... 600/547; 600/382
(58) Field of Classification Search
USPC .......................................... 600/382, 393, 547
See application file for complete search history.

(56) References Cited

U.S. PATENT DOCUMENTS

2008/0021349 A1 1/2008 Sakai et al.
2009/0024053 A1 1/2009 Kasahara

FOREIGN PATENT DOCUMENTS

| JP | A-2002-369806 | 12/2002 |
|---|---|---|
| JP | A-2005-288023 | 10/2005 |
| JP | A-2007-14664 | 1/2007 |
| JP | A-2008-23232 | 2/2008 |
| JP | A-2008-49114 | 3/2008 |
| JP | A-2008-228890 | 10/2008 |
| JP | A-2008-228996 | 10/2008 |
| JP | A-2008-237571 | 10/2008 |
| JP | A-2009-22482 | 2/2009 |
| JP | A-2009-225854 | 10/2009 |
| JP | A-2010-69248 | 4/2010 |
| WO | WO 2008/123042 A1 | 10/2008 |
| WO | WO 2010/032837 A1 | 3/2010 |

OTHER PUBLICATIONS

Sep. 13, 2011 International Search Report issued in Application No. PCT/JP2011/064285 (with translation).

*Primary Examiner* — Max Hindenburg
(74) *Attorney, Agent, or Firm* — Oliff PLC

(57) ABSTRACT

A body fat measurement device includes a trunk area dimension measurement unit in which is provided a trunk area dimension detection unit for detecting a dimension of a measurement subject's trunk area. The trunk area dimension measurement unit has a frame shape that can be disposed surrounding the measurement subject's trunk area, and includes a base portion whose position relative to the trunk area does not change in a state where the trunk area dimension measurement unit is disposed surrounding the trunk area, and a mobile portion that is attached in a movable state to the base portion and whose position relative to the trunk area can change in a state where the trunk area dimension measurement unit is disposed surrounding the trunk area. The trunk area dimension detection unit includes at least a non-contact range sensor provided in the mobile portion.

7 Claims, 16 Drawing Sheets

BODY FAT MEASUREMENT DEVICE

This is a Continuation of PCT Application No. PCT/JP2011/064285 filed Jun. 22, 2011, which claims the benefit of Japanese Patent Application No. 2010-182359, filed on Aug. 17, 2010. The disclosure of the prior application is hereby incorporated by reference herein in its entirety.

TECHNICAL FIELD

The present invention relates to body fat measurement devices configured to be capable of calculating a body fat mass of a measurement subject by measuring a body impedance, and particularly relates to body fat measurement devices configured to be capable of measuring a body fat mass such as a visceral fat mass with ease.

BACKGROUND ART

In recent years, body fat mass is gaining attention as an indicator used to determine the health of a measurement subject. In particular, visceral fat mass is gaining attention as an indicator for determining whether or not a person is suffering from central obesity. Central obesity is said to bring about lifestyle-related diseases that can easily lead to artery hardening, such as diabetes, hypertension, and hyperlipidemia, and the stated indicators hold promise in terms of preventing such diseases. "Visceral fat" refers to fat that accumulates around the internal organs on the inner side of the abdominal muscles and the back muscles, and is distinct from the subcutaneous fat that is located toward the surface of the trunk area. It is typical to employ the area occupied by visceral fat in a cross-section of the trunk area that corresponds to the navel (referred to as a "visceral fat cross-sectional area" hereinafter) as an indicator of the visceral fat mass.

Normally, visceral fat mass is measured by analyzing images obtained through X-ray computed tomography (CT), magnetic resonance imaging (MRI), or the like. In such image analysis, the visceral fat cross-sectional area is calculated geometrically from a tomographic image of the trunk area obtained by using X-ray CT, MRI, or the like. However, it is necessary to use several pieces of large equipment installed in a medical facility, such as X-ray CT, MRI, or other machines, in order to make use of such a measurement method; thus it is extremely difficult to measure visceral fat mass on a daily basis through such a measurement method. X-ray CT also poses the problem of exposure to radiation, and thus cannot necessarily be called a desirable measurement method.

A body impedance technique is being considered as an alternative to these measurement methods. The body impedance technique is a method for measuring body fat mass widely used in household-based body fat measurement devices; in this technique, electrodes are placed in contact with the four limbs, the body impedance is measured using those electrodes, and the body fat mass is calculated from the measured body impedance. The stated household body fat measurement device makes it possible to accurately measure the extent of body fat buildup throughout the entire body or in specific areas such as the four limbs, the trunk area, or the like.

However, conventional body fat measurement devices that use the body impedance technique measure the extent of body fat buildup throughout the entire body or in specific areas such as the four limbs, the trunk area, or the like, as mentioned earlier, and are not capable of accurately extracting and measuring the extent of visceral fat buildup, the extent of subcutaneous fat buildup, and the like individually. This is because, as mentioned above, conventional body fat measurement devices are configured so that the electrodes are attached only to the four limbs, and thus the visceral fat and subcutaneous fat cannot be accurately measured individually.

Accordingly, bringing electrodes into direct contact with the trunk area, measuring the body impedance using those electrodes, and individually and accurately calculating the visceral fat mass and the subcutaneous fat mass based on that measurement is being considered as a way to solve this problem.

For example, JP 2002-369806A (Patent Literature 1) discloses a body fat measurement device configured so that electrodes are provided on the inner circumferential surface of a belt member and the belt member is wrapped around and anchored to the trunk area of a measurement subject, thus placing the electrodes in contact with the trunk area.

Meanwhile, JP 2005-288023A (Patent Literature 2), JP 2008-23232A (Patent Literature 3), JP 2008-237571A (Patent Literature 4), and so on disclose body fat measurement devices configured so that electrodes are provided on the surface of a fitting unit that is fitted to the abdominal area of a measurement subject and the fitting unit is pressed against the abdominal area, thus placing the electrodes in contact with the abdominal area.

Furthermore, JP 2007-14664A (Patent Literature 5) discloses a body fat measurement device configured so that the device is divided into a fitting unit that is fitted to the abdominal area of a measurement subject and a platform unit for the measurement subject to stand upon, where abdominal area electrodes are provided on the surface of the fitting unit, hand electrodes are provided on a handle portion of the fitting unit, and foot electrodes are provided on the stated platform unit; the hand electrodes are placed in contact with the measurement subject's palms by the measurement subject gripping the handle portion of the fitting unit, the abdominal area electrodes are placed in contact with the abdominal area by the measurement subject pressing the fitting unit against his or her abdominal area using the hands that grip the handle portion, and the foot electrodes are placed in contact with the soles of the measurement subject's feet by the measurement subject standing upon the platform unit.

In addition, although not discussing a specific device configuration, JP 2008-228890A (Patent Literature 6) mentions being able to accurately measure visceral fat mass and subcutaneous fat mass by placing electrodes in contact with the back of a measurement subject's trunk area (that is, the back) without placing electrodes in contact with the measurement subject's abdominal area and placing electrodes in contact with the hands and feet of the measurement subject, measuring the body impedance, and calculating the visceral fat mass and the subcutaneous fat mass based on the measured body impedance. One of the reasons for this is that the subcutaneous fat that accumulates on the abdominal area side is relatively thinner than the subcutaneous fat that accumulates on the back area side, and thus if the electrodes are placed in contact with the abdominal area, the current that is applied will flow through fat-free areas, which makes it easy for errors to occur.

Meanwhile, to make it possible to measure the visceral fat mass, subcutaneous fat mass, and so on with a high degree of accuracy using the stated body impedance, it is necessary to take actual measurements of the measurement subject's body build, such as the circumferential length of the trunk area, the trunk area width, and the trunk area depth, and use the measurements in computation processes for calculating the body fat mass.

For example, according to the body fat measurement device disclosed in the stated JP 2005-288023A, a fitting unit that is fitted to a measurement subject's abdominal area is provided upon a pair of arm portions, which make contact with both sides of the measurement subject's trunk area (in other words, both flanks), so that the fitting unit is mobile; the trunk area width is measured by bringing the arm portions into contact with both flanks, and the result of that actual measurement is used in computation processes for calculating body fat mass.

In addition, according to the body fat measurement device disclosed in the stated JP 2008-23232A, a fitting unit that is fitted to a measurement subject's abdominal area is provided upon an arm portion, which makes contact with the measurement subject's back, so that the fitting unit is mobile; the trunk area depth is measured by bringing the arm portion into contact with the back, and the result of that actual measurement is used in computation processes for calculating body fat mass.

Furthermore, according to the body fat measurement device disclosed in the stated JP 2008-237571A, a trunk area width measurement unit disposed at a distance from the outside of both sides of the measurement subject's trunk area is configured separate from a fitting unit that is fitted to the measurement subject's abdominal area, and multiple non-contact range sensors are provided in the trunk area width measurement unit so as to take an actual measurement of the trunk area width; the result of that actual measurement is used in computation processes for calculating body fat mass.

Furthermore, although the technique does not bring electrodes into contact with a measurement subject's trunk area, JP 2009-22482A (Patent Literature 7) discloses a body fat measurement device in which foot electrodes are provided on a platform unit onto which the measurement subject steps, a trunk area width measurement unit disposed at a distance from the outside of both sides of the measurement subject's trunk area is supported on a support column portion that extends upward from the stated platform unit while the measurement subject stands on the platform unit, and multiple non-contact range sensors are provided in the trunk area width measurement unit so as to take an actual measurement of the trunk area width; the result of that actual measurement is used in computation processes for calculating body fat mass.

CITATION LIST

Patent Literature

Patent Literature 1: JP 2002-369806A
Patent Literature 2: JP 2005-288023A
Patent Literature 3: JP 2008-23232A
Patent Literature 4: JP 2008-237571A
Patent Literature 5: JP 2007-14664A
Patent Literature 6: JP 2008-228890A
Patent Literature 7: JP 2009-22482A

SUMMARY OF INVENTION

Technical Problem

Here, as described above, it is necessary to take an accurate actual measurement of the trunk area width and trunk area depth in order to calculate the visceral fat mass with a high degree of accuracy using the body impedance technique.

However, with the body fat measurement devices disclosed in the aforementioned JP 2005-288023A and JP 2008-23232A, in the case where actual measurements of the trunk area width and the trunk area depth are to be taken by bringing the arm portions provided in a mobile state into contact with the trunk area, the measurement subject or the like is forced to carry out operations for individually moving the arm portions along two directions of the trunk area, or the forward/backward direction and the right/left direction; thus there is a problem in that the body fat measurement device is not necessarily easy to use. These operations become extremely complicated particularly in the case where the body fat measurement device is configured so that the measurement subject him/herself can perform the measurement alone, without the help of an assistant or the like; this greatly inhibits taking measurements of a visceral fat mass or the like in a simple and easy manner.

On the other hand, in the case where the configuration is such that actual measurements of the trunk area width and trunk area depth are taken using multiple non-contact range sensors, as with the body fat measurement devices disclosed in the aforementioned JP 2008-237571A and JP 2009-22482A, although complex operations are rendered unnecessary and a highly-usable device can be implemented as described, there is a problem in that the use of many non-contact range sensors increases the number of components, which in turn leads to a major increase in manufacturing costs.

Having been achieved in order to solve the stated problems, it is an object of the present invention to provide a body fat measurement device that is capable of accurately measuring body fat masses such as visceral fat mass and that is easy to operate and use when taking such measurements, and that can be manufactured for a low cost.

Solution to Problem

A body fat measurement device according to the present invention includes a plurality of electrodes, a body impedance measurement unit, a trunk area dimension detection unit, a trunk area dimension measurement unit, and a body fat mass calculation unit. The plurality of electrodes make contact with predetermined areas of the surface of a measurement subject's body. The body impedance measurement unit is a unit that measures a body impedance of the measurement subject's body using the plurality of electrodes. The trunk area dimension detection unit is a unit for detecting a trunk area dimension of the measurement subject. The trunk area dimension measurement unit is a frame-shaped unit in which the trunk area dimension detection unit is provided and that is capable of being disposed so as to surround the measurement subject's trunk area. The body fat mass calculation unit is a unit that calculates a body fat mass based on the body impedance measured by the body impedance measurement unit and the trunk area dimension detected by the trunk area dimension detection unit. The trunk area dimension measurement unit includes a base portion whose position relative to the measurement subject's trunk area does not change in a state where the trunk area dimension measurement unit is disposed surrounding the measurement subject's trunk area, and a mobile portion that is attached in a movable state to the base portion and whose position relative to the measurement subject's trunk area can change in a state where the trunk area dimension measurement unit is disposed surrounding the measurement subject's trunk area. The trunk area dimension detection unit includes at least a non-contact range sensor provided in the mobile portion.

In the stated body fat measurement device according to the present invention, it is preferable for the mobile portion to be configured to be capable of moving along at least one of a trunk area width direction and a trunk area depth direction in a state where the trunk area dimension measurement unit is disposed surrounding the measurement subject's trunk area, and for the trunk area dimension detection unit to detect at least one of a trunk area width and a trunk area depth of the measurement subject based on distance information detected by the range sensor while the mobile portion is moving.

In the stated body fat measurement device according to the present invention, the trunk area dimension detection unit may further include a movement amount detection sensor that detects an amount by which the mobile portion moves. In this case, it is preferable for the mobile portion to be configured to be capable of moving along one of a trunk area width direction and a trunk area depth direction in a state where the trunk area dimension measurement unit is disposed surrounding the measurement subject's trunk area; and for the trunk area dimension detection unit to detect one of a trunk area width and a trunk area depth of the measurement subject based on distance information detected by the range sensor while the mobile portion is moving, and to detect the other of the trunk area width and the trunk area depth of the measurement subject based on movement amount information detected by the movement amount detection sensor. Furthermore, in this case, wherein the trunk area dimension detection unit may detect the other of the trunk area width and the trunk area depth of the measurement subject based on the distance information detected by the range sensor while the mobile portion is moving in addition to the movement amount information detected by the movement amount detection sensor.

It is preferable for the stated body fat measurement device according to the present invention to further include a biasing member that biases the mobile portion toward one side of the direction in which the mobile portion moves.

It is preferable for the stated body fat measurement device according to the present invention to further include a control unit that controls the operations of the body impedance measurement unit, the trunk area dimension detection unit, and the body fat mass calculation unit; in this case, it is preferable for the control unit to carry out control for driving the body impedance measurement unit to start measuring the body impedance after the trunk area dimension has been detected by the trunk area dimension detection unit.

In the body fat measurement device according to the present invention, it is preferable for the plurality of electrodes to include trunk area electrodes for making contact with the surface of the measurement subject's trunk area. In this case, the trunk area electrodes may be disposed below the measurement subject's trunk area when the measurement subject is lying down, and the trunk area dimension measurement unit may be disposed so as to surround the measurement subject's trunk area when the measurement subject is lying down; alternatively, the trunk area electrodes may be provided on the base portion of the trunk area dimension measurement unit.

In the body fat measurement device according to the present invention, it is preferable for the plurality of electrodes to include back area electrodes for making contact with the surface of a back area that corresponds to an area of the measurement subject's trunk area on the back side thereof.

In the body fat measurement device according to the present invention, it is preferable for the body fat mass calculation unit to include at least one of a visceral fat mass calculation unit that calculates the visceral fat mass of the measurement subject and a subcutaneous fat mass calculation unit that calculates the subcutaneous fat mass of the measurement subject.

Advantageous Effects of Invention

According to the present invention, it is possible to realize a body fat measurement device that is capable of accurately measuring body fat masses such as visceral fat mass and that is easy to operate and use when taking such measurements, and that can be manufactured at a low cost.

DESCRIPTION OF EMBODIMENTS

Figure 1A:
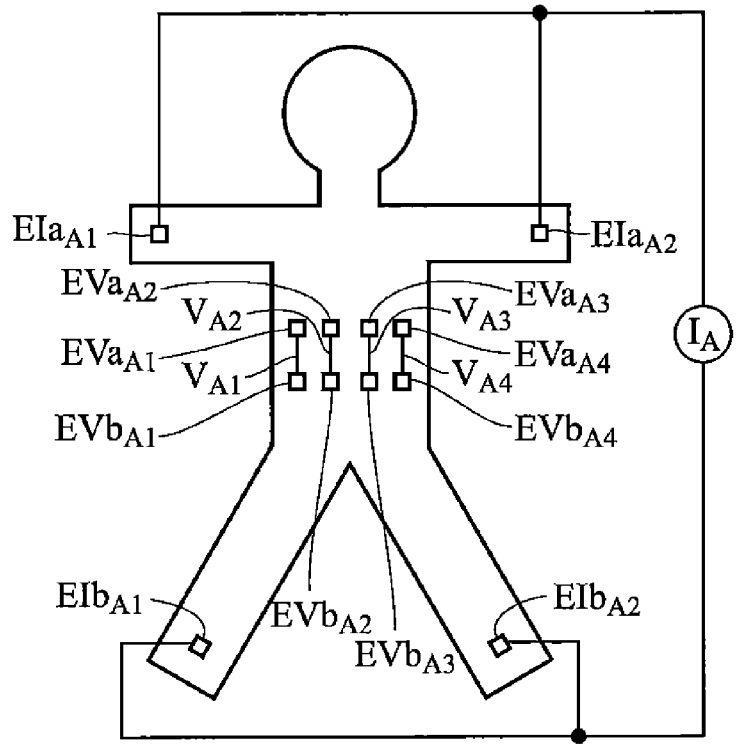
FIG. 1A is schematic a diagram illustrating the fundamentals of measurement performed by a body fat measurement device according to a first embodiment of the present invention.

Hereinafter, embodiments of the present invention will be described in detail with reference to the drawings. In the following, a first embodiment and variations thereon illustrate examples in which the present invention is applied in a body fat measurement device configured to take measurements with a measurement subject lying face-up, whereas a second embodiment illustrates an example in which the present invention is applied in a body fat measurement device configured to take measurements with the measurement subject standing. Note that in the following embodiments and variations thereon, identical or corresponding elements are given the same reference numerals in the drawings, and individual descriptions thereof will not be repeated.

Before describing the various embodiments of the present invention and the variations thereon, definitions will first be given for terms expressing parts of the body. "Trunk area" refers to the area excluding the head, neck, and four limbs, and corresponds to the trunk of the body. "Back area" refers to the area located on the back side of the stated trunk area, and corresponds to the area of the stated trunk area excluding the abdominal area side and the chest area side. "Back area surface" refers to the entire body surface of the back area, and indicates the surface of the trunk area that can be seen when a measurement subject is observed from the back side. Meanwhile, "body axis" refers to an axis located along the direction in which the trunk area extends, or in other words, an axis extending in a direction approximately perpendicular to a side cross-section of the measurement subject's trunk area. "Trunk area width" corresponds to a dimension that is orthogonal to the body axis and that spans from the left to right ends of a horizontal cross-section of the trunk area, whereas "trunk area depth" corresponds to a dimension that is orthogonal to the body axis and that spans from the front to the back ends of a horizontal cross-section of the trunk area. "Trunk area dimension", meanwhile, refers to either or both of the stated "trunk area width" and "trunk area depth". Note that it is preferable for the stated cross-section employed when determining the aforementioned "trunk area width" and "trunk area depth" to be a horizontal cross-section at an area of the trunk area that corresponds to the position of the navel.

First Embodiment

Figure 1B:
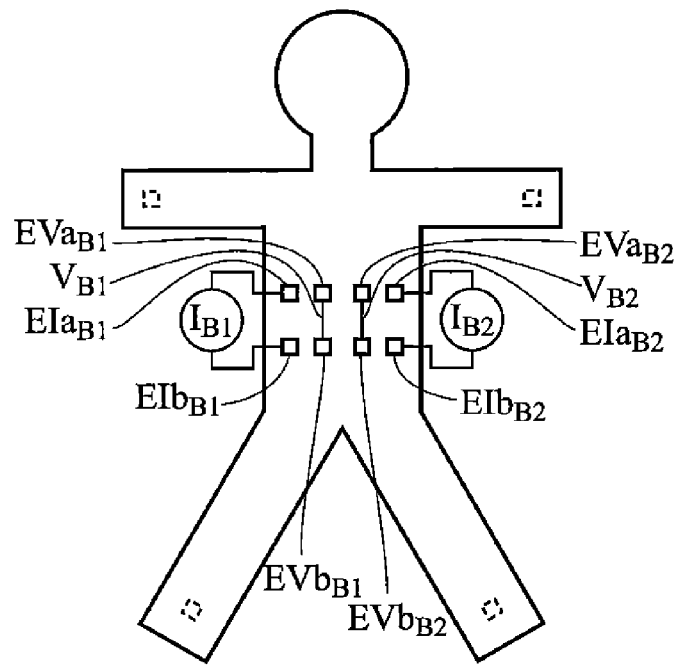
FIG. 1B is schematic a diagram illustrating the fundamentals of measurement performed by a body fat measurement device according to the first embodiment of the present invention.

FIGS. 1A and 1B are schematic diagrams illustrating the fundamentals of measurement performed by a body fat measurement device according to a first embodiment of the present invention. Here, FIG. 1A is a diagram illustrating the placement of electrodes when obtaining a body impedance for the entire trunk area, whereas FIG. 1B is a diagram illustrating the placement of electrodes when obtaining a body impedance for a surface layer area on the back area side of the trunk area. First, the fundamentals of measurement performed by the body fat measurement device according to the present embodiment will be described with reference to FIGS. 1A and 1B. Note that FIGS. 1A and 1B both illustrate the measurement subject from the back side thereof.

As shown in FIG. 1A, electrodes $EIa_{A1}$ and $EIa_{A2}$ are attached to the surface of the left arm of the measurement subject and the surface of the right arm of the measurement subject, respectively, in order to obtain the body impedance for the entire trunk area. Likewise, electrodes $EIb_{A1}$ and $EIb_{A2}$ are attached to the surface of the left leg of the measurement subject and the surface of the right leg of the measurement subject, respectively. Four pairs of electrodes are attached to the back area surface of the measurement subject, with each pair disposed so as to follow the body axis direction, and with the four pairs arranged in the widthwise direction of the trunk area. In other words, as shown in FIG. 1A, a total of eight electrodes, or electrodes $EVa_{A1}$, $EVb_{A1}$, $EVa_{A2}$, $EVb_{A2}$, $EVa_{A3}$, $EVb_{A3}$, $EVa_{A4}$, and $EVb_{A4}$, are attached to the back area surface of the measurement subject.

In this state, a constant current IA that passes through the trunk area is applied to the measurement subject using the electrodes $EIa_{A1}$, $EIa_{A2}$, $EIb_{A1}$, and $EIb_{A2}$ attached to both arms and both legs, respectively. While the constant current IA is applied, a potential difference $V_{A1}$ is detected using the pair of electrodes $EVa_{A1}$ and $EVb_{A1}$ attached to the back area surface, a potential difference $V_{A2}$ is detected using the pair of electrodes $EVa_{A2}$ and $EVb_{A2}$ attached to the back area surface, a potential difference $V_{A3}$ is detected using the pair of electrodes $EVa_{A3}$ and $EVb_{A3}$ attached to the back area surface, and a potential difference $V_{A4}$ is detected using the pair of electrodes $EVa_{A4}$ and $EVb_{A4}$ attached to the back area surface.

A body impedance Zt of the entire trunk area is calculated from the potential differences $V_{A1}$, $V_{A2}$, $V_{A3}$, and $V_{A4}$ detected in this manner. Note that if the body impedance Zt is found at this time by calculating the average value of the four stated potential differences $V_{A1}$, $V_{A2}$, $V_{A3}$, and $V_{A4}$, it is possible to reduce the influence of variations in the fat distribution within the trunk area.

In this state, the constant current IA is flowing between both arms and both legs, which are positioned at a distance from the trunk area, and thus almost all of the applied constant current IA passes through areas of low electrical resistance, or in other words, through areas aside from fat. Accordingly, the stated body impedance Zt calculated from the potential differences $V_{A1}$, $V_{A2}$, $V_{A3}$, and $V_{A4}$ measured using the constant current IA is greatly influenced by the amount of non-fat areas (internal organs, muscle, and bone) within the trunk area. Accordingly, the area occupied by non-fat areas (called a "non-fat cross-sectional area" hereinafter) Sa in the cross-section of the trunk area in an area corresponding to the location of the navel can be estimated based on the stated body impedance Zt.

Meanwhile, as shown in FIG. 1B, the four pairs of electrodes are attached to the back area surface of the measurement subject with each pair disposed so as to follow the body axis direction, and with the four pairs arranged in the widthwise direction of the trunk area, in order to obtain the body impedance of the surface layer area on the back area side of the trunk area. In other words, as shown in FIG. 1B, a total of eight electrodes, or electrodes $EIa_{B1}$, $EIb_{B1}$, $EVa_{B1}$, $EVb_{B1}$, $EVa_{B2}$, $EVb_{B2}$, $EIa_{B2}$, and $EIb_{B2}$, are attached to the back area surface of the measurement subject.

In this state, a constant current $I_{B1}$ that passes through the back area locally is applied to the measurement subject using the pair of electrodes $EIa_{B1}$ and $EIb_{B1}$, and a constant current $I_{B2}$ that passes through the back area locally is applied to the measurement subject using the pair of electrodes $EIa_{B2}$ and $EIb_{B2}$. While the constant currents $I_{B1}$ and $I_{B2}$ are applied, a potential difference $V_{B1}$ is detected using the pair of electrodes $EVa_{B1}$ and $EVb_{B1}$ attached to the back area surface, and a potential difference $V_{B2}$ is detected using the pair of electrodes $EVa_{B2}$ and $EVb_{B2}$ attached to the back area surface. Here, the current values of the two constant currents $I_{B1}$ and $I_{B2}$ applied to the measurement subject are set to the same value.

A body impedance Zs of the surface layer area on the back area side of the trunk area is calculated form the potential differences $V_{B1}$ and $V_{B2}$ calculated in this manner. Note that if the body impedance Zs is found at this time by calculating the average value of the two stated potential differences $V_{B1}$ and $V_{B2}$, it is possible to reduce the influence of variations in the fat distribution within the surface layer area in the back area of the trunk area. Note that potential differences can also be measured in four locations by switching circuits so that the electrodes to which the current was applied serve as electrodes for detecting the potential differences and the electrodes that were detecting the potential differences serve as electrodes for current application. Doing so makes it possible to further reduce the influence of variations in the subcutaneous fat and so on.

In this state, the constant currents $I_{B1}$ and $I_{B2}$ are applied locally to the back area of the trunk area, and thus almost all of both the applied constant currents $I_{B1}$ and $I_{B2}$ pass through the surface layer area of the back area. Accordingly, the stated body impedance Zs calculated from the potential differences $V_{B1}$ and $V_{B2}$ measured using the constant currents $I_{B1}$ and $I_{B2}$ is greatly influenced by the subcutaneous fat mass. Accordingly, the subcutaneous fat cross-sectional area (called a "subcutaneous fat cross-sectional area" hereinafter) Sb in the cross-section of the trunk area including the location of the navel can be estimated based on the stated body impedance Zs.

Next, an example of a computation process for calculating a visceral fat mass using the stated body impedances Zt and Zs obtained in this manner will be described.

If the overall area of the cross-section of the trunk area at the area corresponding to the location of the navel (called a "trunk area cross-sectional area" hereinafter) is taken as St, a visceral fat cross-sectional area Sx can be calculated through the following Formula (1) using the trunk area cross-sectional area St, the non-fat cross-sectional area Sa, and the subcutaneous fat cross-sectional area Sb.

$$Sx = St - Sa - Sb \qquad \text{Formula (1)}$$

Here, the trunk area cross-sectional area St can be calculated using the circumferential length of the trunk area (the so-called waist length), the width of the trunk area, the depth of the trunk area, and so on. For example, in the case where the trunk area cross-sectional area St is to be calculated from the width and depth of the trunk area, assuming that the width of the trunk area is taken as 2×a and the depth of the trunk area is taken as 2×b, and because the trunk area has a generally oval cross-sectional shape, the trunk area cross-sectional area St can be approximated through the following Formula (2).

$$St = \pi \times a \times b \qquad \text{Formula (2)}$$

However, the trunk area cross-sectional area St approximated through the above Formula (2) is highly likely to contain a significant degree of error, and it is thus preferable to find a more accurate trunk area cross-sectional area St by multiplying that trunk area cross-sectional area St by a coefficient α for reducing error. This coefficient α is obtained, for example, by finding the optimum value for α that fulfills St'=α×π×a×b, from the relationship between the stated a and b and a trunk area cross-sectional area St' obtained from a sample of a large number of X-ray CT images.

Accordingly, the stated Formula (2) can approximate with a lower degree of error through the following Formula (3) by using the coefficient α.

$$St = \alpha \times \pi \times a \times b \qquad \text{Formula (3)}$$

Note that it is preferable to optimize the coefficient α multiplied for correction as described above as appropriate in accordance with information such as the measurement subject's sex, age, height, weight, and so on (hereinafter, this information will be referred to collectively as "measurement subject information"). In other words, the trunk area cross-sectional area St can be approximated with a higher degree of accuracy by changing the value of the stated coefficient α in accordance with the measurement subject information.

As described above, the non-fat cross-sectional area Sa can be calculated based on the body impedance Zt of the entire trunk area. However, the non-fat cross-sectional area Sa cannot be accurately calculated using only the body impedance Zt of the entire trunk area. That is, the non-fat cross-sectional area Sa tends to be proportional to the size of the trunk area, and thus it is necessary to further convert the value obtained from the body impedance Zt in order to calculate the non-fat cross-sectional area Sa. Accordingly, the non-fat cross-sectional area Sa can be expressed through, for example, the following Formula (4).

$$Sa = \beta \times a \times (1/Zt) \qquad \text{Formula (4)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, β represents a coefficient for converting the body impedance Zt of the entire trunk area into the non-fat cross-sectional area Sa, and an optimum value can be found, for example, based on a sample of a large number of X-ray CT images, in the same manner as when finding the coefficient α. In other words, the optimum value for β that fulfils Sa'=β×a×

(1/Zt) can be found from the relationship between a non-fat cross-sectional area Sa' obtained from a sample of a large number of X-ray CT images, the body impedance Zt of the entire trunk area of the measurement subject imaged by the X-ray CT, and the stated a.

Note that it is preferable for the stated coefficient β to be optimized as appropriate in accordance with the measurement subject information, in the same manner as the coefficient α mentioned above. In other words, the non-fat cross-sectional area Sa can be approximated with a higher degree of accuracy by changing the value of the stated coefficient β in accordance with the measurement subject information.

Furthermore, as described above, the subcutaneous fat cross-sectional area Sb can be calculated based on the body impedance Zs of the surface layer area on the back area side of the trunk area. However, the subcutaneous fat cross-sectional area Sb cannot be accurately calculated using only the body impedance Zs of the surface layer area on the back area side of the trunk area. That is, the subcutaneous fat cross-sectional area Sb tends to be proportional to the size of the trunk area, and thus it is necessary to further convert the value obtained from the body impedance Zs in order to calculate the subcutaneous fat cross-sectional area Sb. Accordingly, the subcutaneous fat cross-sectional area Sb can be expressed through, for example, the following Formula (5).

$$Sb = \gamma \times a \times Zs \quad \text{Formula (5)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, γ represents a coefficient for converting the body impedance Zs of the surface layer area on the back area side of the trunk area into the subcutaneous fat cross-sectional area Sb, and an optimum value can be found, for example, based on a sample of a large number of X-ray CT images, in the same manner as when finding the coefficient α or the coefficient β. In other words, the optimum value for γ that fulfils Sb'·γ×a×Zs can be found from the relationship between a subcutaneous fat cross-sectional area Sb' obtained from a sample of a large number of X-ray CT images, the body impedance Zs of the surface layer area on the back area side of the trunk area of the measurement subject imaged by the X-ray CT, and the stated a.

Note that it is preferable for the stated coefficient γ to be optimized as appropriate in accordance with the measurement subject information, in the same manner as the coefficient α and the coefficient β mentioned above. In other words, the subcutaneous fat cross-sectional area Sb can be approximated with a higher degree of accuracy by changing the value of the stated coefficient γ in accordance with the measurement subject information.

As described thus far, in the body fat measurement device according to the present embodiment, the visceral fat cross-sectional area Sx is calculated based on the stated Formula (1) using the trunk area cross-sectional area St, the non-fat cross-sectional area Sa calculated based on the body impedance Zt of the entire trunk area, and the subcutaneous fat cross-sectional area Sb calculated based on the body impedance Zs of the surface layer area on the back area side of the trunk area; more specifically, the visceral fat cross-sectional area Sx is calculated based on the following Formula (6) by substituting the stated Formula (3) through Formula (5) in the stated Formula (1).

$$Sx = \alpha \times \pi \times a \times b - \beta \times a \times (1/Zt) - \gamma \times a \times Zs \quad \text{Formula (6)}$$

Figure 2:
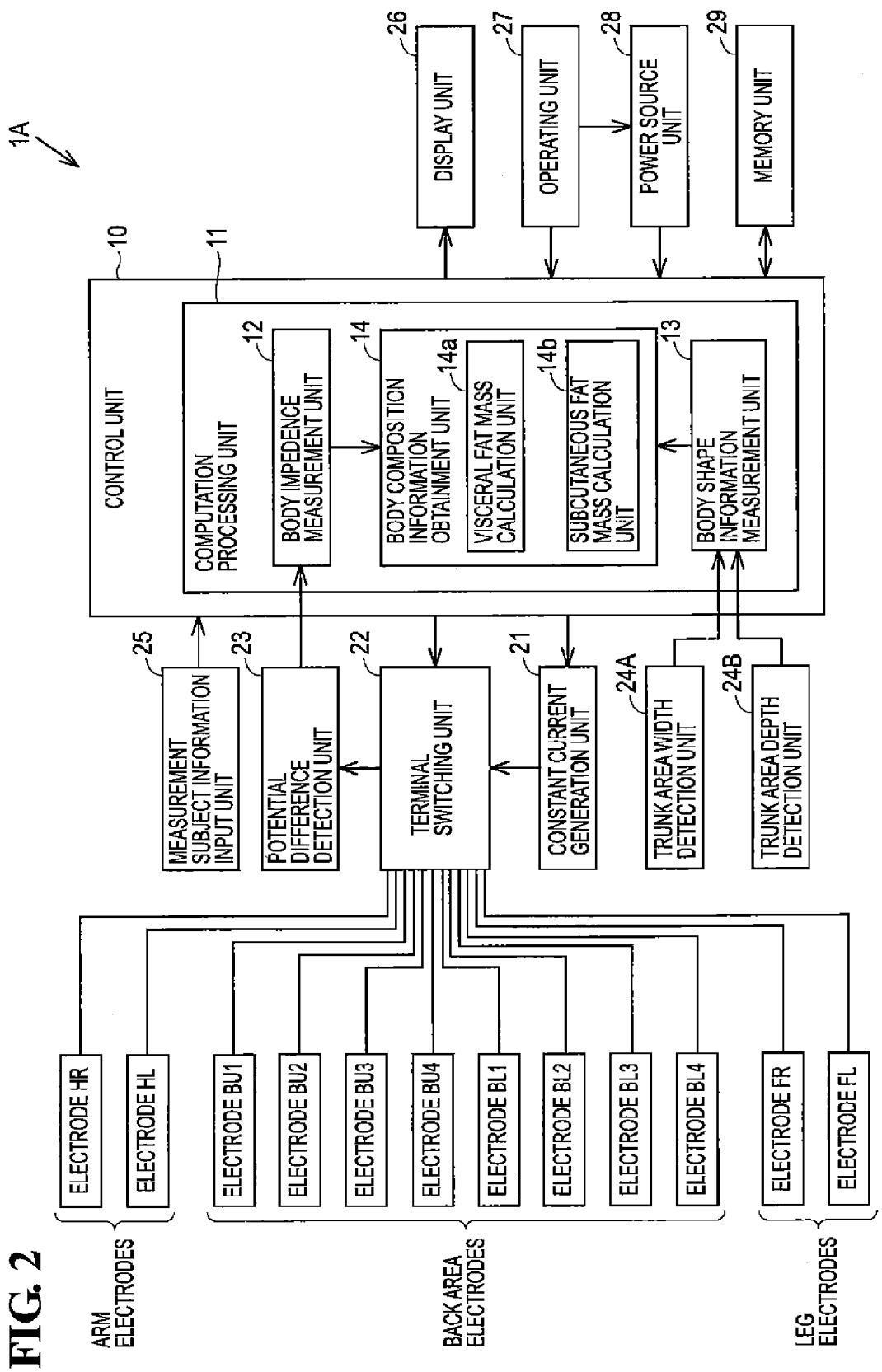
FIG. 2 is a block diagram illustrating the functional block configuration of the body fat measurement device according to the first embodiment of the present invention.

FIG. 2 is a block diagram illustrating the functional block configuration of the body fat measurement device according to the present embodiment. Next, the functional block configuration of the body fat measurement device according to the present embodiment will be described with reference to FIG. 2.

As shown in FIG. 2, a body fat measurement device 1A according to the present embodiment includes: a control unit 10; a constant current generation unit 21; a terminal switching unit 22; a potential difference detection unit 23; a trunk area width detection unit 24A; a trunk area depth detection unit 24B; a measurement subject information input unit 25; a display unit 26; an operating unit 27; a power source unit 28; a memory unit 29; and multiple electrodes HR, HL, BU1-BU4, BL1-BL4, FR, and FL that are fitted to the body of the measurement subject. The control unit 10 includes a computation processing unit 11, and the computation processing unit 11 has a body impedance measurement unit 12, a body shape information measurement unit 13, and a body composition information obtainment unit 14.

The control unit 10 is configured of, for example, a CPU (Central Processor Unit), and is a unit for controlling the body fat measurement device 1A as a whole. Specifically, the control unit 10 outputs instructions to the various aforementioned functional blocks, accepts inputs of various types of information from the various aforementioned functional blocks, performs various types of computation processes based on the various types of information accepted, and so on. The various types of computation processes are carried out by the stated computation processing unit 11 provided in the control unit 10.

The aforementioned multiple electrodes include: arm electrodes HR and HL serving as upper limb electrodes placed in contact with surfaces of the upper limbs of the measurement subject; back area electrodes BU1-BU4 and BL1-BL4 placed in contact with the back area surface of the measurement subject; and leg electrodes FR and FL serving as lower limb electrodes placed in contact with surfaces of the lower limbs of the measurement subject. Of these, the arm electrodes HR and HL are placed in contact with measurement subject's wrists, and the leg electrodes FR and FL are placed in contact with the measurement subject's ankles. Meanwhile, as shown in FIGS. 1A and 1B, the back area electrodes BU1-BU4 and BL1-BL4 are arranged in rows and placed in contact with the back area surface of the measurement subject. Note that the arm electrodes HR and HL, back area electrodes BU1-BU4 and BL1-BL4, and leg electrodes FR and FL are all electrically connected to the aforementioned terminal switching unit 22.

The terminal switching unit 22 is configured of, for example, a relay circuit; based on instructions inputted from the control unit 10, the terminal switching unit 22 electrically connects specific electrodes selected from the stated multiple electrodes to the constant current generation unit 21 and electrically connects specific electrodes selected from the stated multiple electrodes to the potential difference detection unit 23. Through this, the electrodes electrically connected to the constant current generation unit 21 by the terminal switching unit 22 function as constant current application electrodes, and the electrodes electrically connected to the potential difference detection unit 23 by the terminal switching unit 22 function as potential difference detection electrodes. In other words, by the terminal switching unit 22 operating based on instructions inputted from the control unit 10, the multiple electrodes HR, HL, BU1-BU4, BL1-BL4, FR, and FL respectively function as either the respective electrodes $EIa_{A1}$, $EIa_{A2}$, $EIb_{A1}$, $EIb_{A2}$, $EVa_{A1}$, $EVb_{A1}$, $EVa_{A2}$, $EVb_{A2}$, $EVa_{A3}$, $EVb_{A3}$, $EVa_{A4}$, and $EVb_{A4}$ shown in FIG. 1A or the respective electrodes $EIa_{B1}$, $EIb_{B1}$, $EVa_{B1}$, $EVb_{B1}$, $EVa_{B2}$, $EVb_{B2}$, $EIa_{B2}$, and $EIb_{B2}$ shown in FIG. 1B.

The constant current generation unit 21 generates a constant current based on an instruction inputted from the control unit 10, and supplies the generated constant current to the stated constant current application electrodes via the terminal switching unit 22. A high-frequency current (for example, 50 kHz, 500 μA) that can be used effectively for measuring body composition information is selected as the constant current generated by the constant current generation unit 21. Through this, the constant current can be applied to the measurement subject via the constant current application electrodes.

The potential difference detection unit 23 detects a potential difference between the electrodes electrically connected to the potential difference detection unit 23 by the terminal switching unit 22 (that is, the potential difference detection electrodes), and outputs the detected potential difference to the control unit 10. Through this, the potential difference between the potential difference detection electrodes is detected in a state in which the aforementioned constant current is applied to the measurement subject.

The trunk area width detection unit 24A is a detection unit for measuring the width of the measurement subject's trunk area without making contact therewith, and is configured of, for example, a range sensor such as a photoelectric sensor. Meanwhile, the trunk area depth detection unit 24B is a detection unit for measuring the depth of the measurement subject's trunk area, and is configured of, for example, movement amount detection sensor that employs various types of encoders, a non-contact range sensor such as a photoelectric sensor, or the like. In the present embodiment, a movement amount detection sensor that employs various types of encoders is used as the trunk area depth detection unit 24B. The trunk area width detection unit 24A and the trunk area depth detection unit 24B output signals based on the values detected to the body shape information measurement unit 13. Note that in addition to photoelectric sensors, various types of non-contact range sensors that utilize ultrasound waves, electromagnetic waves, and the like (light of various wavelength bands, including laser light and visible light, radio waves, magnetism, electrical fields, and so on) can be used as the stated range sensors.

The measurement subject information input unit 25 is a unit for obtaining information regarding the measurement subject used in computation processes carried out by the computation processing unit 11, and is configured of, for example, keys and the like that can be depressed by the measurement subject. Here, the measurement subject information includes at least one of the sex, age, height, weight, and so on of the measurement subject, as mentioned above. The measurement subject information input unit 25 accepts the input of measurement subject information, and outputs the accepted measurement subject information to the control unit 10. Note that the measurement subject information input unit 25 is not absolutely necessary in the configuration of the present invention, and whether or not to provide the measurement subject information input unit 25 can be determined based on whether or not it is necessary to use the measurement subject information in the computation processes performed by the computation processing unit 11.

The computation processing unit 11 includes the body impedance measurement unit 12, the body shape information measurement unit 13, and the body composition information obtainment unit 14, as mentioned above. The body composition information obtainment unit 14 functions as a body fat mass calculation unit, and includes a visceral fat mass calculation unit 14a and a subcutaneous fat mass calculation unit 14b. The body impedance measurement unit 12 calculates the body impedance based on a signal inputted from the potential difference detection unit 23, and outputs that body impedance to the body composition information obtainment unit 14. The body shape information measurement unit 13 calculates the width and the depth of the measurement subject's trunk area based on the signals inputted from the trunk area width detection unit 24A and the trunk area depth detection unit 24B, and outputs the calculated information to the body composition information obtainment unit 14. The body composition information obtainment unit 14 calculates and obtains the body composition information based on the body impedance inputted from the body impedance measurement unit 12, the width and depth of the trunk area inputted from the body shape information measurement unit 13, and in some cases, the measurement subject information inputted from the measurement subject information input unit 25 as well. More specifically, the visceral fat mass calculation unit 14a calculates a visceral fat mass and the subcutaneous fat mass calculation unit 14b calculates a subcutaneous fat mass.

The display unit 26 is configured of, for example, an LCD (Liquid Crystal Display) or the like, and displays the body composition information calculated by the body composition information obtainment unit 14 as mentioned above. More specifically, the visceral fat mass calculated by the visceral fat mass calculation unit 14a and the subcutaneous fat mass calculated by the subcutaneous fat mass calculation unit 14b are displayed in the display unit 26 based on signals outputted from the control unit 10. Here, with the body fat measurement device 1A according to the present embodiment, the visceral fat mass is displayed as, for example, the visceral fat cross-sectional area, and the subcutaneous fat mass is displayed as, for example, the subcutaneous fat cross-sectional area.

The operating unit 27 is a unit through which the measurement subject inputs commands to the body fat measurement device 1A, and is configured of, for example, buttons and the like that can be depressed by the measurement subject. Note that the operating unit 27 includes various types of operation buttons such as a power button, a measure button, and so on.

The power source unit 28 is a unit for supplying electrical power to the control unit 10, and uses an internal power source such as a battery, an external power source such as an AC outlet, or the like.

The memory unit 29 is configured of, for example, a random access memory (RAM) or a read-only memory (ROM), and is a unit for storing various types of data, programs, and the like for the body fat measurement device 1A. The memory unit 29 stores, for example, the aforementioned measurement subject information, the calculated body composition information, a body composition information measurement program for executing a body composition information measurement process (mentioned latex), and so on.

Figure 3:
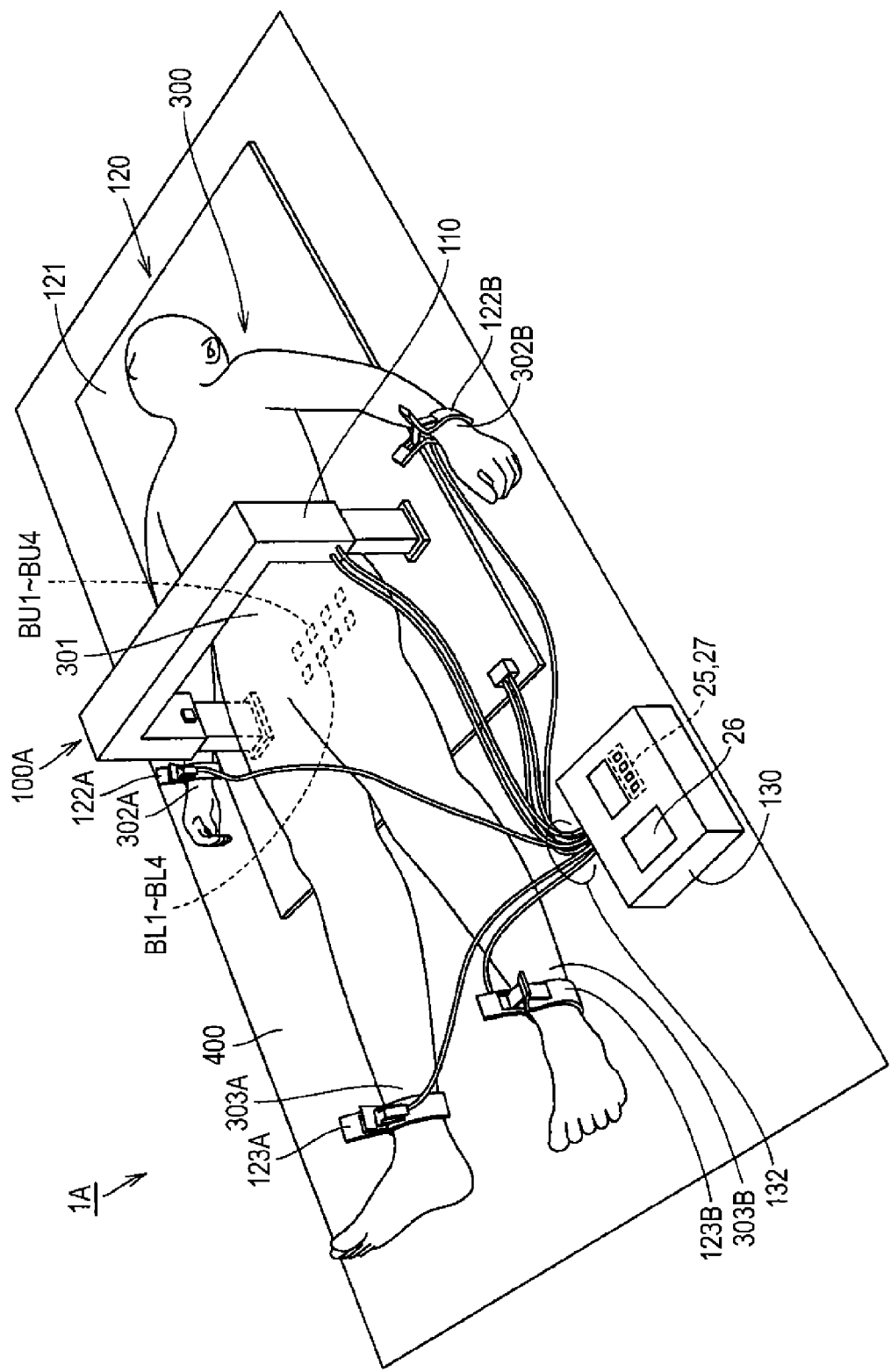
FIG. 3 is a perspective view illustrating the configuration of a body fat measurement device and a measurement position according to a first embodiment of the present invention.
Figure 4:
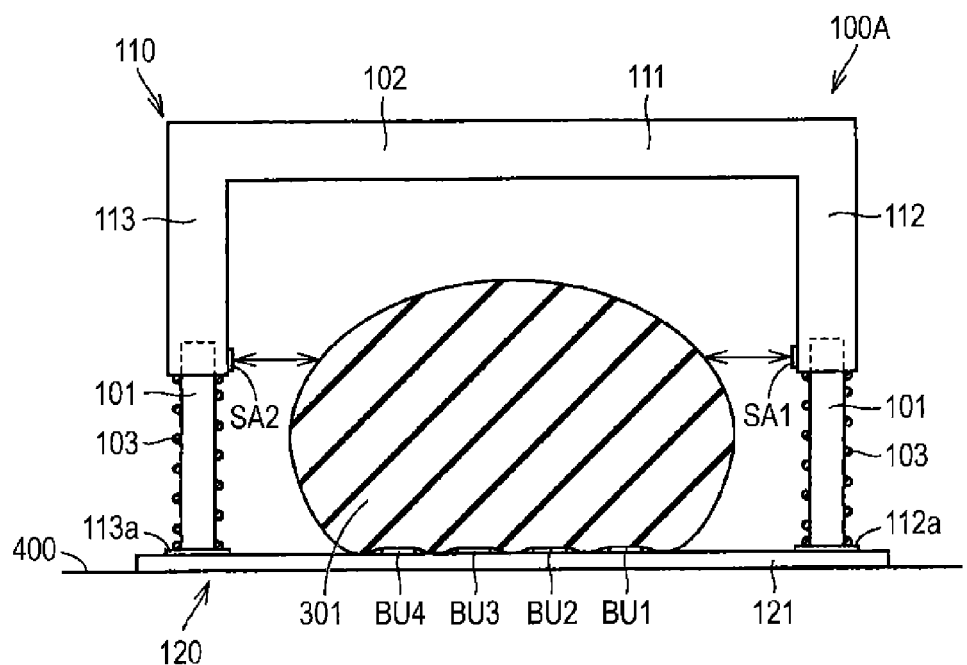
FIG. 4 is a schematic diagram illustrating the configuration of a trunk area dimension measurement unit in the body fat measurement device according to the first embodiment of the present invention, and a method for measuring a trunk area width and a trunk area depth using the stated unit.
Figure 5:
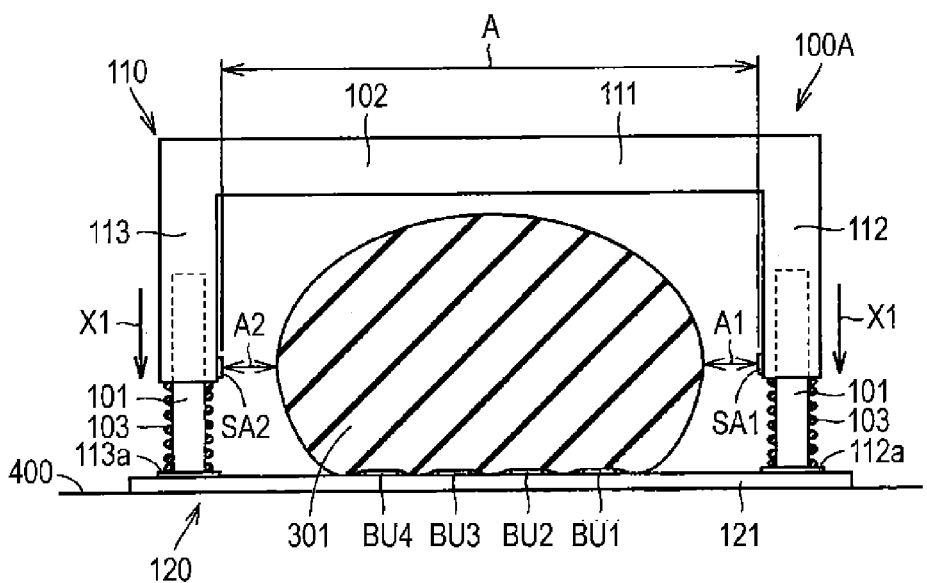
FIG. 5 is a schematic diagram illustrating a method for measuring a trunk area width and a trunk area depth using the trunk area dimension measurement unit in the body fat measurement device according to the first embodiment of the present invention.
Figure 6:
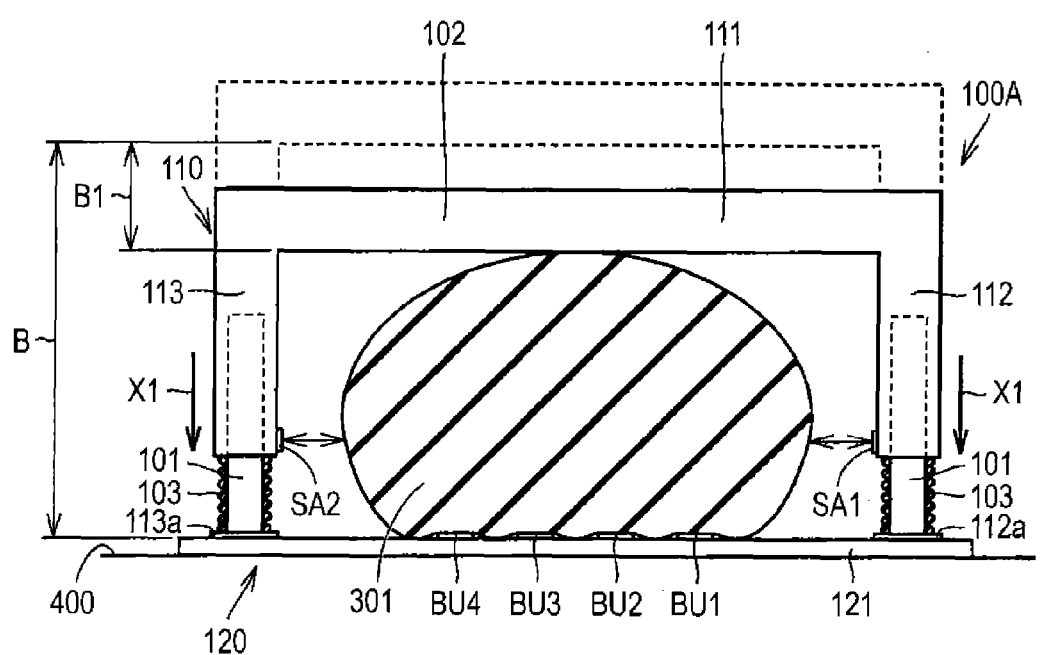
FIG. 6 is a schematic diagram illustrating a method for measuring a trunk area width and a trunk area depth using the trunk area dimension measurement unit in the body fat measurement device according to the first embodiment of the present invention.
Figure 7:
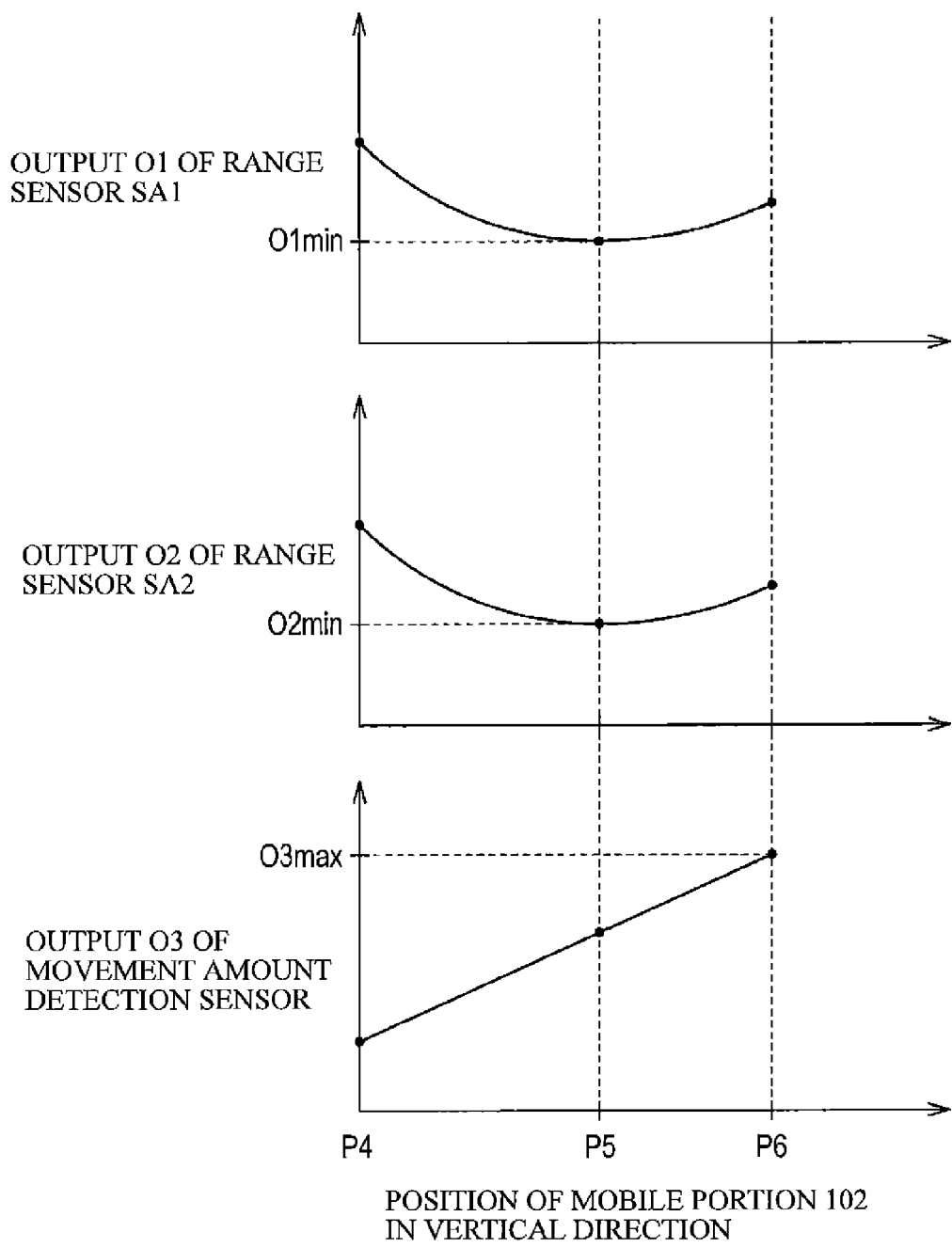
FIG. 7 is a diagram illustrating outputs of range sensors and a movement amount detection sensor provided in the body fat measurement device according to the first embodiment of the present invention.

FIG. 3 is a perspective view illustrating the configuration of the body fat measurement device and a measurement position according to the present embodiment. FIG. 4 is a schematic diagram illustrating the configuration of a trunk area dimension measurement unit in the body fat measurement device according to the present embodiment, and a method for measuring a trunk area width and a trunk area depth using the stated unit. FIGS. 5 and 6 are schematic diagrams illustrating a method for measuring a trunk area width and a trunk area depth using the trunk area dimension measurement unit in the body fat measurement device according to the present embodiment. FIG. 7 is a diagram illustrating outputs of range sensors and a movement amount detection sensor provided in the body fat measurement device according to the present embodiment. Next, the configuration of the body fat measurement device according to the present embodiment, the measurement position, the configuration of the trunk area dimension measurement unit, a method for measuring the trunk area width and the trunk area depth using the stated device/unit, and so on will be described with reference to FIGS. 3 through 7.

First, the configuration of the body fat measurement device and the configuration of the trunk area dimension measurement unit according to the present embodiment will be described with reference to FIGS. 3 and 4.

As shown in FIG. 3, the body fat measurement device 1A according to the present embodiment primarily includes a trunk area dimension measurement unit 100A, a back area electrode support unit 120, a right arm fitting unit 122A, a left arm fitting unit 122B, a right leg fitting unit 123A, a left leg fitting unit 123B, and a main body unit 130. The aforementioned various functional blocks are provided in these units 100A, 120, 122A, 122B, 123A, 123B, and 130. The main body unit 130 is electrically connected to each of the remaining other units 100A, 120, 122A, 122B, 123A, and 123B by connection cables 132, and exchanges signals with the aforementioned various functional blocks via the connection cables 132.

The main body unit 130 is configured of a box-shaped unit on the top surface of which the measurement subject information input unit 25, the operating unit 27, the display unit 26, and so on are provided, and includes the stated control unit 10, constant current generation unit 21, terminal switching unit 22, potential difference detection unit 23, power source unit 28, memory unit 29, and so on.

The back area electrode support unit 120 is configured of a sheet-shaped unit that can be placed upon a bed surface 400 in an unrolled state, and includes an insulative mat 121 and the back area electrodes BU1-BU4 and BL1-13L4 that are disposed upon a primary surface of the mat 121. The back area electrodes BU1-BU4 and BL1-BL4 are arranged in rows and columns on the mat 121, and are provided protruding slightly from the primary surface of the mat 121, so as to make contact with the back area surface on a trunk area 301 of a measurement subject 300 with certainty when the measurement subject 300 is in a position lying face-up on the mat 121. Note that the back area electrodes BM1-BU4 and BL1-BL4 provided in the back area electrode support unit 120 are all connected to the terminal switching unit 22 provided in the main body unit 130 via the connection cables 132.

The right arm fitting unit 122A and the left arm fitting unit 122B are each configured of clip-shaped units, and are fitted onto a right arm 302A and a left arm 302B, respectively, of the measurement subject 300 during measurement. The arm electrode HR is provided in the right arm fitting unit 122A, and the arm electrode HL is provided in the left arm fitting unit 122B. The arm electrodes HR and HL are provided in the right arm fitting unit 122A and the left arm fitting unit 122B, respectively, in an exposed manner, so as to make contact with the surfaces of the right arm and the left arm of the measurement subject 300 when the right arm fitting unit 122A and the left arm fitting unit 122B are fitted to the right arm 302A and the left arm 302B, respectively. Note that the arm electrodes FIR and HL provided in the right arm fitting unit 122A and the left arm fitting unit 122B are both connected to the terminal switching unit 22 provided in the main body unit 130 via the connection cables 132.

The right leg fitting unit 123A and the left leg fitting unit 123B are each configured of clip-shaped units, and are fitted onto a right leg 303A and a left leg 303B, respectively, of the measurement subject 300 during measurement. The leg electrode FR is provided in the right leg fitting unit 123A, and the leg electrode FL is provided in the left leg fitting unit 123B. The leg electrodes FR and FL are provided in the right leg fitting unit 123A and the left leg fitting unit 123B, respectively, in an exposed manner, so as to make contact with the surfaces of the right leg and the left leg of the measurement subject 300 when the right leg fitting unit 123A and the left leg fitting unit 123B are fitted to the right leg 303A and the left leg 303B, respectively. Note that the leg electrodes FR and FL provided in the right leg fitting unit 123A and the left leg fitting unit 123B are all connected to the terminal switching unit 22 provided in the main body unit 130 via the connection cables 132.

As shown in FIGS. 3 and 4, the trunk area dimension measurement unit 100A is configured of a gate-type unit having a frame shape that is capable of surrounding the trunk area 301 of the measurement subject 300 who is in a position lying face-up on the bed surface 400. More specifically, the trunk area dimension measurement unit 100A is configured of a frame member 110 that includes a bar-shaped upper frame portion 111, a bar-shaped right side frame portion 112, and a bar-shaped left side frame portion 113; the unit includes a pair of base portions 101 whose positions relative to the trunk area 301 of the measurement subject 300 do not change when the unit is disposed surrounding the trunk area 301 of the measurement subject 300, and a mobile portion 102 attached in a movable state to the stated pair of base portions 101 so that the position of the mobile portion 102 can change relative to the trunk area 301 of the measurement subject 300 when the unit is disposed surrounding the trunk area 301 of the measurement subject 300.

The pair of base portions 101 are configured toward the lower ends of the right side frame portion 112 and the left side frame portion 113, respectively, and leg portions 112a and 113a are provided on the lower ends of the pair of base portions 101, respectively. The leg portions 112a and 113a are sections for enabling the trunk area dimension measurement unit 100A to be placed upon the bed surface 400 in a stable state. The mobile portion 102 is configured of the entire upper frame portion 111 and the areas of the right side frame portion 112 and the left side frame portion 113 toward the top ends thereof, and is attached to the base portions 101 so as to be capable of moving in the vertical direction (that is, in the trunk area depth direction).

Elastic members 103 (not shown in FIG. 3; see FIG. 4) configured of springs or the like and serving as biasing members are provided on the outsides of the pair of base portions 101, and the elastic members 103 are interposed and held between the mobile portion 102 and the leg portions 112a and 113a. The elastic members 103 are members for biasing the mobile portion 102 upward, and in the case where the mobile portion 102 has been pushed downward from a default position shown in FIG. 4, are for returning the mobile portion 102 to the default position by pushing the mobile portion 102 upward.

As shown in FIG. 4, range sensors SA1 and SA2, serving as the stated trunk area width detection unit 24A, are attached to the inner surface sides of the respective areas of the right side frame portion 112 and the left side frame portion 113 that correspond to the mobile portion 102 of the trunk area dimension measurement unit 100A (that is, the surfaces of the trunk area dimension measurement unit 100A on the sides that face the trunk area 301 of the measurement subject 300 when the trunk area dimension measurement unit 100A is disposed surrounding the trunk area 301 of the measurement subject 300). Both of the range sensors SA1 and SA2 emit light toward the inner side of the trunk area dimension measurement unit 100A along the horizontal direction, and measure distances from the range sensors SA1 and SA2 to the trunk area 301 of the measurement subject 300, which is the area to be detected, by receiving light reflected therefrom.

The range sensors SA1 and SA2 are provided in positions toward the lower ends of the stated mobile portion 102, and move in the vertical direction along with the mobile portion 102 when the mobile portion 102 moves in the vertical direction. Here, the range sensors SA1 and SA2 are disposed in positions on the sides of the trunk area 301 of the measurement subject 300 when the mobile portion 102 is in the default position shown in FIG. 4. Note that the range sensors SA1 and SA2 provided in the trunk area dimension measurement unit 100A are all connected to the control unit 10 provided in the main body unit 130 via the connection cables 132.

Meanwhile, a movement amount detection sensor (not shown in FIG. 4 and the like), serving as the stated trunk area depth detection unit 24B, is attached to the trunk area dimension measurement unit 100A. The movement amount detection sensor detects the amount by which the mobile portion 102 has moved from the default position in the case where the mobile portion 102 has been pushed down against the biasing force of the aforementioned elastic members 103. Note that the movement amount detection sensor provided in the trunk area dimension measurement unit 100A is connected to the control unit 10 provided in the main body unit 130 via the connection cables 132.

Next, a measurement position to be assumed by the measurement subject when measuring a body fat mass such as a visceral fat mass using the body fat measurement device according to the present embodiment will be described with reference to FIG. 3.

As shown in FIG. 3, during measurement, the measurement subject 300 lies face-up on the back area electrode support unit 120 that has been unrolled and placed upon the bed surface 400. At this time, the location in which the measurement subject 300 lies is adjusted so that the back area surface makes contact with the back area electrodes BU1-BU4 and BL1-BL4 provided in the back area electrode support unit 120. Then, the measurement subject 300 fits the right arm fitting unit 122A and the left atm fitting unit 122B to the wrist of the right arm 302A and the wrist of the left arm 302B, respectively, and fits the right leg fitting unit 123A and the left leg fitting unit 123B to the ankle of the right leg 303A and the ankle of the left leg 303B, respectively.

In this state, the trunk area dimension measurement unit 100A is disposed around the trunk area 301 at an area that corresponds to the location of the navel, and the trunk area width and trunk area depth are measured using the trunk area dimension measurement unit 100A. After this, the body impedance is measured using the electrodes HR, HL, BU1-BU4, BL1-BL4, FR, and FL provided in the back area electrode support unit 120, the right arm fitting unit 122A, the left arm fitting unit 122B, the right leg fitting unit 123A, and the left leg fitting unit 123B.

Next, a method for measuring the trunk area width and the trunk area depth using the trunk area dimension measurement unit provided in the body fat measurement device according to the present embodiment will be described with reference to FIGS. 4 through 7.

FIGS. 4 through 6 are diagrams illustrating, in stages, a state in which the mobile portion 102 is moved downward (in the drawings, the direction of an arrow X1) in order to measure the trunk area dimensions. Here, FIG. 4 illustrates a state in which the mobile portion 102 is in the default position; FIG. 5 illustrates a state in which the range sensors SA1 and SA2 are opposed to the left and right ends of the trunk area 301 of the measurement subject 300 as a result of the mobile portion 102 being pushed downward; and FIG. 6 illustrates a state in which the mobile portion 102 has been pushed further downward and has reached a position in which the mobile portion 102 cannot move any further.

Meanwhile, FIG. 7 is a graph illustrating relationships between the position of the mobile portion 102 in the vertical direction and an output O1 of the range sensor SA1, an output O2 of the range sensor SA2, and an output O3 of the movement amount detection sensor; in FIG. 7, the positions of the mobile portion 102 illustrated in the aforementioned FIGS. 4 through 6 are respectively indicated as P4 through P6. Note that with respect to FIG. 7, sensors in which the outputs decrease as the detected distance increases are used for the range sensors SA1 and SA2, whereas a sensor in which the output increases as the detected amount of movement increases is used for the movement amount detection sensor.

The trunk area width is calculated from the outputs O1 and O2 of the range sensors SA1 and SA2, outputted while the mobile portion 102 is moving. As shown in FIGS. 4 through 6, when the range sensors SA1 and SA2 are positioned to the left and right of the trunk area 301 of the measurement subject 300, the light emitted from the range sensors SA1 and SA2 is emitted toward the right side surface of the trunk area 301 of the measurement subject 300 (that is, the surface of the right flank) and the left side surface of the trunk area 301 of the measurement subject 300 (that is, the surface of the left flank), respectively. Accordingly, as shown in FIG. 7, the outputs O1 and O2 from the range sensors SA1 and SA2 outputted while the mobile portion 102 is moving are outputs based on the respective distances from the range sensors SA1 and SA2 to the trunk area 301 of the measurement subject 300 in the horizontal direction.

Accordingly, as shown in FIG. 5, a trunk area width 2×a of the measurement subject 300 is calculated based on the following Formula (7) using distances A1 and A2 that are distances based on minimum values O1min and O2min (see FIG. 7) of the outputs of the range sensors SA1 and SA2 (A1: the distance between the range sensor SA1 and the end of the right side surface of the trunk area 301 of the measurement subject 300; A2: the distance between the range sensor SA2 and the end of the left side surface of the trunk area 301 of the measurement subject 300), and a predetermined distance A (that is, the distance between the range sensor SA1 and the range sensor SA2).

$$2\times a = A - A1 - A2 \qquad \text{Formula (7)}$$

On the other hand, the trunk area depth is calculated from the output O3 of the movement amount detection sensor, outputted while the mobile portion 102 is moving. As shown in FIG. 6, the mobile portion 102 makes contact with the top surface of the trunk area 301 of the measurement subject 300 as a result of being pushed downward, and thus does not move any further downward when in such a state of contact.

Accordingly, as shown in FIG. 6, a trunk area depth 2×b of the measurement subject 300 is calculated based on the following Formula (8) using a distance 131, which is a distance based on a maximum value O3max (see FIG. 7) of the output of the movement amount detection sensor while the mobile portion 102 is moving, and a predetermined distance B (a distance between the upper frame portion 111 of the mobile portion 102 and the top surface of the mat 121 in the back area electrode support unit 120 when the mobile portion 102 is in the default position).

$$2 \times b = B - B1 \qquad \text{Formula (8)}$$

In this manner, the body fat measurement device 1A according to the present embodiment is configured so that the trunk area width and the trunk area depth can be measured by the two range sensors SA1 and SA2 and the one movement amount detection sensor provided in the trunk area dimension measurement unit 100A. To be more specific, in the body fat measurement device 1A according to the present embodiment, the mobile portion 102 is attached to the base portions 101 so that the mobile portion 102 is capable of moving along the trunk area depth direction, the trunk area width detection unit 24A is configured of the stated two range sensors SA1 and SA2 provided in predetermined positions on the mobile portion 102, the trunk area depth detection unit 24B is configured of the stated one movement amount detection sensor that detects the amount by which the mobile portion 102 has moved, and as a result, the trunk area width and the trunk area depth can be measured.

Figure 8:
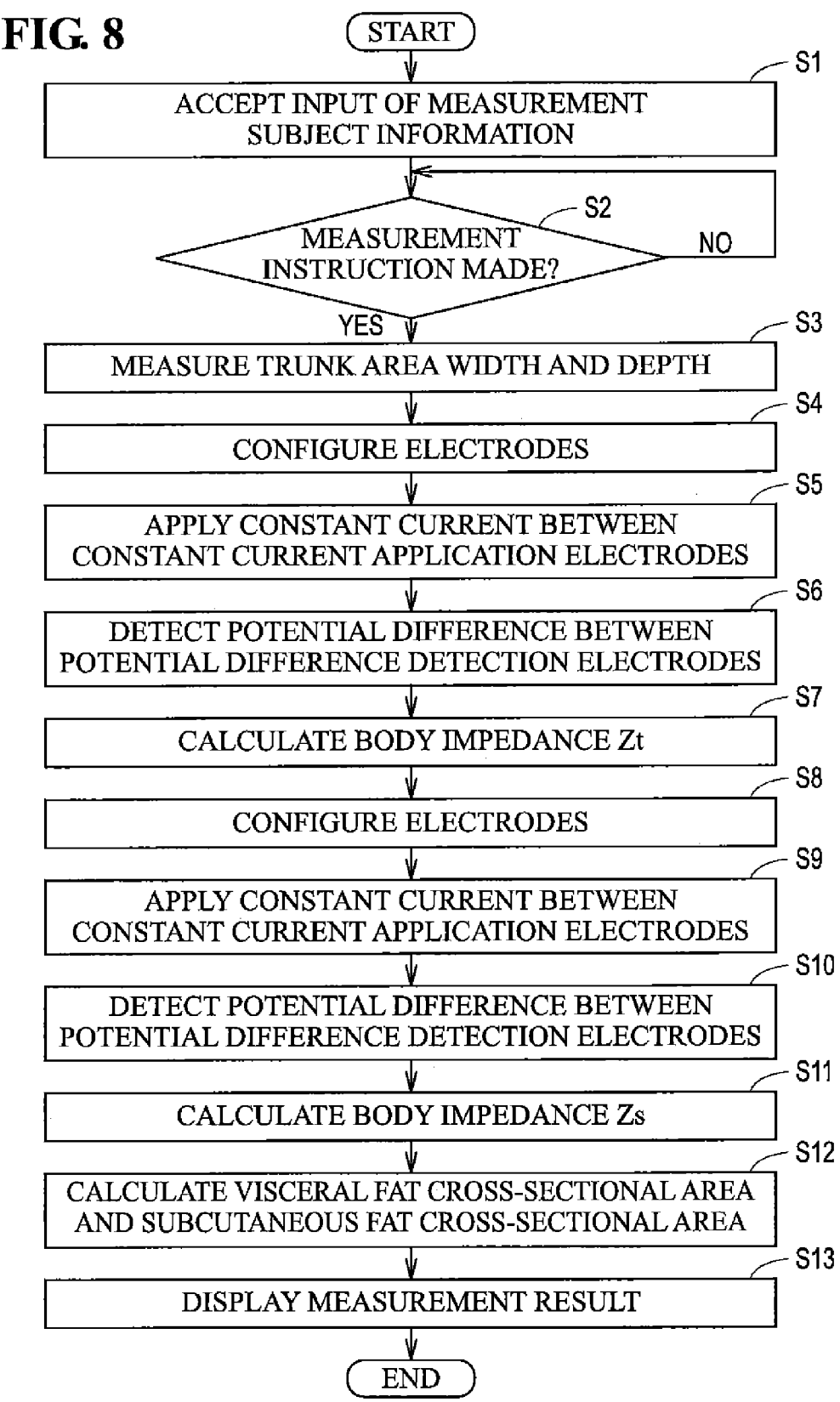
FIG. 8 is a flowchart illustrating a process performed by a control unit in the body fat measurement device according to the first embodiment of the present invention.

FIG. 8 is a flowchart illustrating a process performed by the control unit in the body fat measurement device according to the present embodiment. Next, a sequence of processes executed by the control unit of the body fat measurement device according to the present embodiment will be described with reference to FIG. 8. Note that the processes indicated in the flowchart in FIG. 8 are stored in the memory unit 29 in advance as a program, and a visceral fat cross-sectional area measurement process and a subcutaneous fat cross-sectional area measurement process are realized by the control unit 10 when the control unit 10 including the computation processing unit 11 reads out and executes that program.

As shown in FIG. 8, the control unit 10 first accepts an input of the measurement subject information (step S1). The accepted measurement subject information is temporarily saved in, for example, the memory unit 29.

Next, the control unit 10 determines whether or not there has been an instruction to start the measurement (step S2). The control unit 10 stands by until there has been an instruction to start the measurement (NO in step S2), and advances to the next process in the case where an instruction to start the measurement has been detected (YES in step S2).

Next, the control unit 10 measures the width and depth of the trunk area (step S3). Specifically, the control unit 10 stands by for an operation that moves the mobile portion 102 of the trunk area dimension measurement unit 100A downward, and when such an operation is made, calculates the width 2×a and the depth 2×b of the trunk area 301 of the measurement subject 300 using the body shape information measurement unit 13, based on signals inputted from the trunk area width detection unit 24A and the trunk area depth detection unit 24B. The obtained width 2×a and depth 2×b of the trunk area 301 of the measurement subject 300 are temporarily saved in the memory unit 29. Note that the stated operation may be performed by the measurement subject 300 him/herself, or may be performed by an assistant.

Next, the control unit 10 configures the electrodes (step S4). Specifically, the control unit 10 outputs an instruction to the terminal switching unit 22 for switching the electrodes, and based on this, the terminal switching unit 22 configures the multiple electrodes HR, HL, BU1-BU4, BL1-BL4, FR, and FL to the configuration of the electrodes shown in FIG. 1A.

Next, the control unit 10 applies a constant current between the constant current application electrodes (step S5). Specifically, the control unit 10 outputs an instruction to the constant current generation unit 21 for generating the constant current, and based on this, the constant current generation unit 21 applies the constant current IA generated between the constant current application electrodes as shown in FIG. 1A.

Next, the control unit 10 detects a potential difference between the potential difference detection electrodes (step S6). Specifically, the control unit 10 outputs an instruction to the potential difference detection unit 23 for detecting a potential difference, and based on this, the potential difference detection unit 23 detects the potential differences $V_{A1}$, $V_{A2}$, $V_{A3}$, and $V_{A4}$ between the potential difference detection electrodes shown in FIG. 1A, and outputs the detected potential differences to the body impedance measurement unit 12.

Next, the control unit 10 calculates the body impedance Zt (step S7). Specifically, the control unit 10 calculates the body impedance Zt using the body impedance measurement unit 12, based on a signal inputted from the potential difference detection unit 23. The calculated body impedance Zt is temporarily saved in the memory unit 29.

Next, the control unit 10 reconfigures the electrodes (step S8). Specifically, the control unit 10 outputs an instruction to the terminal switching unit 22 for switching the electrodes, and based on this, the terminal switching unit 22 configures the multiple electrodes HR, HL, BU1-BU4, BL1-BL4, FR, and FL to the configuration of the electrodes shown in FIG. 1B.

Next, the control unit 10 applies a constant current between the constant current application electrodes (step S9). Specifically, the control unit 10 outputs an instruction to the constant current generation unit 21 for generating the constant current, and based on this, the constant current generation unit 21 applies the constant currents $I_{B1}$ and $I_{B2}$ generated between the constant current application electrodes as shown in FIG. 1B.

Next, the control unit 10 detects a potential difference between the potential difference detection electrodes (step S10). Specifically, the control unit 10 outputs an instruction to the potential difference detection unit 23 for detecting a potential difference, and based on this, the potential difference detection unit 23 detects the potential differences $V_{B1}$ and $V_{B2}$ between the potential difference detection electrodes shown in FIG. 1B, and outputs the detected potential differences to the body impedance measurement unit 12.

Next, the control unit 10 calculates the body impedance Zs (step S11). Specifically, the control unit 10 calculates the body impedance Zs using the body impedance measurement unit 12, based on a signal inputted from the potential difference detection unit 23. The calculated body impedance Zs is temporarily saved in the memory unit 29.

Next, the control unit 10 calculates the visceral fat cross-sectional area and the subcutaneous fat cross-sectional area (step S12). Specifically, the control unit 10 calculates the visceral fat cross-sectional area Sx as the visceral fat mass using the visceral fat mass calculation unit 14a and calculates the subcutaneous fat cross-sectional area Sb as the subcutaneous fat mass using the subcutaneous fat mass calculation unit 14b, based on the width 2×a and depth 2×b of the trunk area detected in step S3, the body impedance Zt calculated in step S7, and the body impedance Zs calculated in step S11. Note that the calculated visceral fat cross-sectional area Sx and subcutaneous fat cross-sectional area Sb are temporarily saved in the memory unit 29.

Then, the control unit 10 displays the measurement results (step S13). Specifically, the control unit 10 outputs, to the display unit 26, an instruction to display the visceral fat cross-sectional area Sx and subcutaneous fat cross-sectional area Sb calculated in step S12, and based on this, the display unit 26 displays those measurement results.

Through this, the body fat measurement device 1A completes the visceral fat cross-sectional area measurement process and the subcutaneous fat cross-sectional area measurement process.

With the body fat measurement device 1A according to the present embodiment described thus far, the base portions 101 and the mobile portion 102 are provided in the trunk area dimension measurement unit 100A, and the non-contact range sensors SA1 and SA2 are provided in the mobile portion 102, making it possible to measure the trunk area width. By employing such a configuration, the trunk area width and trunk area depth can be measured with certainty and accurately through an extremely simple operation of pushing the mobile portion 102 downward, without using many sensors; as a result, it is possible to realize a body fat measurement device that is capable of accurately measuring body fat masses such as visceral fat mass and that is easy to operate and use when taking such measurements, and that can be manufactured for a low cost. Moreover, by employing the aforementioned configuration, it is possible for the measurement subject to take measurements by him/herself without help from an assistant or the like, which makes it possible to realize a body fat measurement device that is suited to taking daily measurements of visceral fat masses or the like.

The aforementioned describes a single example of a body fat measurement device where the measurement subject is to assume a face-up position during measurement, in which providing a mobile portion in a trunk area width detection unit and providing non-contact range sensors in the mobile portion makes it possible to realize a body fat measurement device that is capable of accurately measuring body fat masses such as visceral fat mass and that is easy to operate and use when taking such measurements, and that can be manufactured for a low cost; however, the specific configuration is not limited to the aforementioned descriptions, and various other configuration examples are conceivable from the same standpoint. The following will describe some such examples as variations on the aforementioned embodiment.

First Variation

Figure 9:
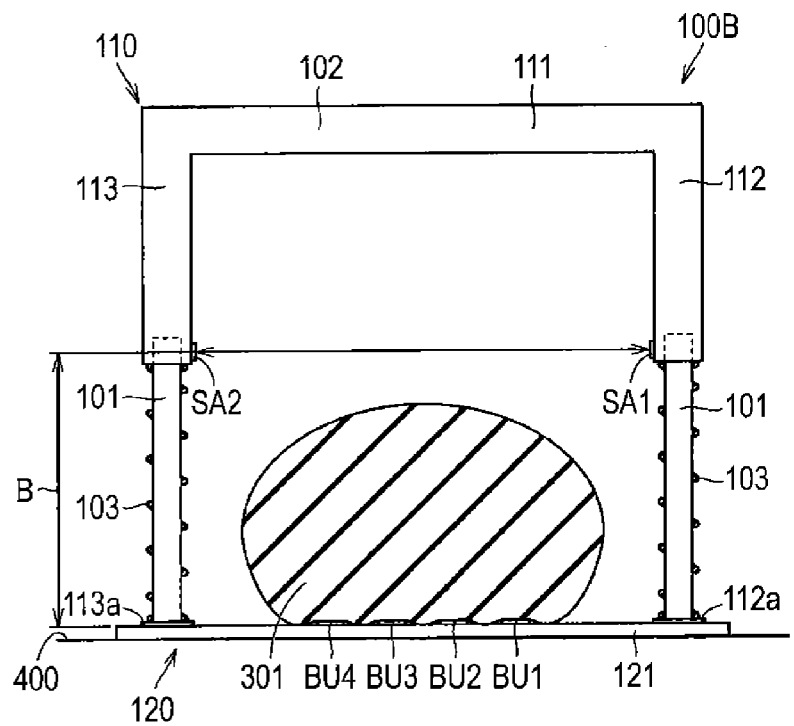
FIG. 9 is a schematic diagram illustrating the configuration of a trunk area dimension measurement unit in a body fat measurement device according to a first variation, and a method for measuring a trunk area width and a trunk area depth using the stated unit.
Figure 10:
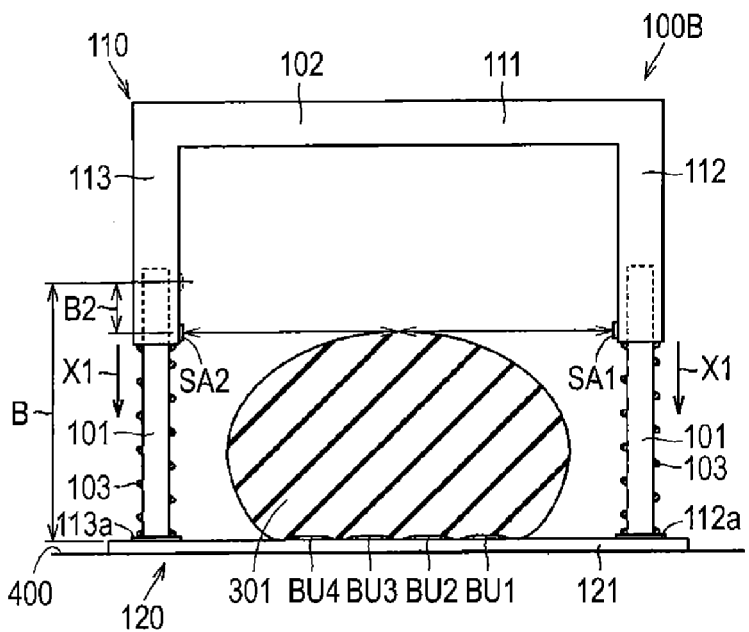
FIG. 10 is a schematic diagram illustrating a method for measuring a trunk area width and a trunk area depth using the trunk area dimension measurement unit in the body fat measurement device according to the first variation.
Figure 11:
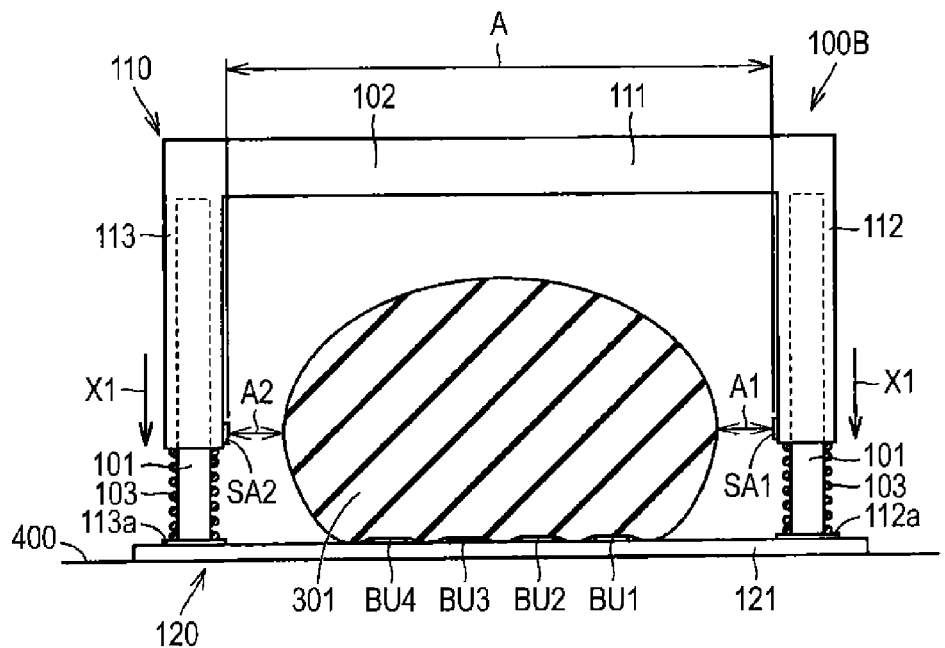
FIG. 11 is a schematic diagram illustrating a method for measuring a trunk area width and a trunk area depth using the trunk area dimension measurement unit in the body fat measurement device according to the first variation.
Figure 12:
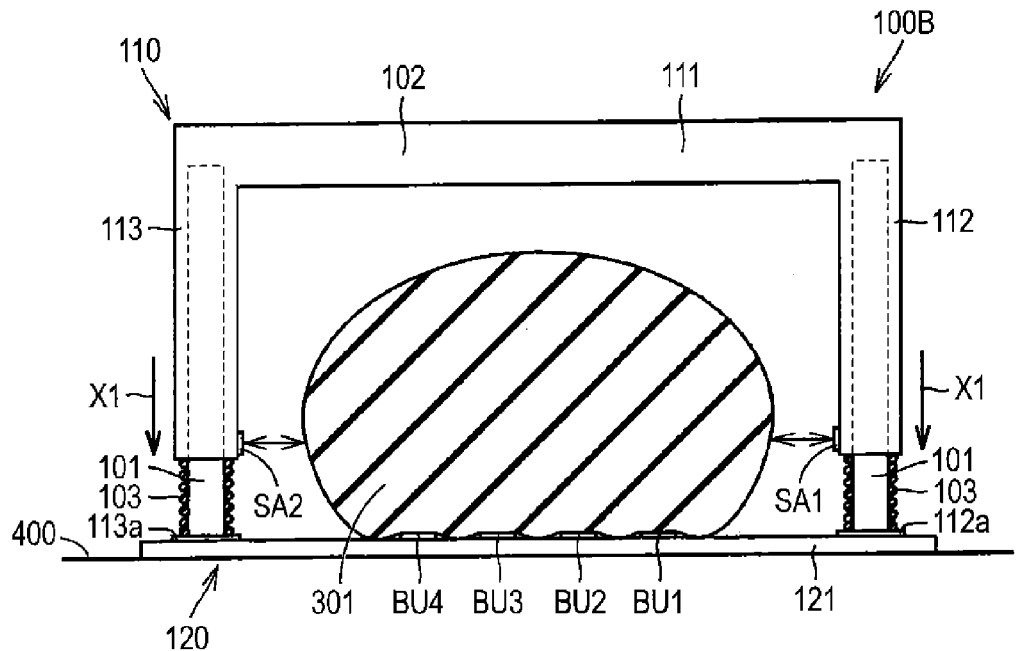
FIG. 12 is a schematic diagram illustrating a method for measuring a trunk area width and a trunk area depth using the trunk area dimension measurement unit in the body fat measurement device according to the first variation.
Figure 13:
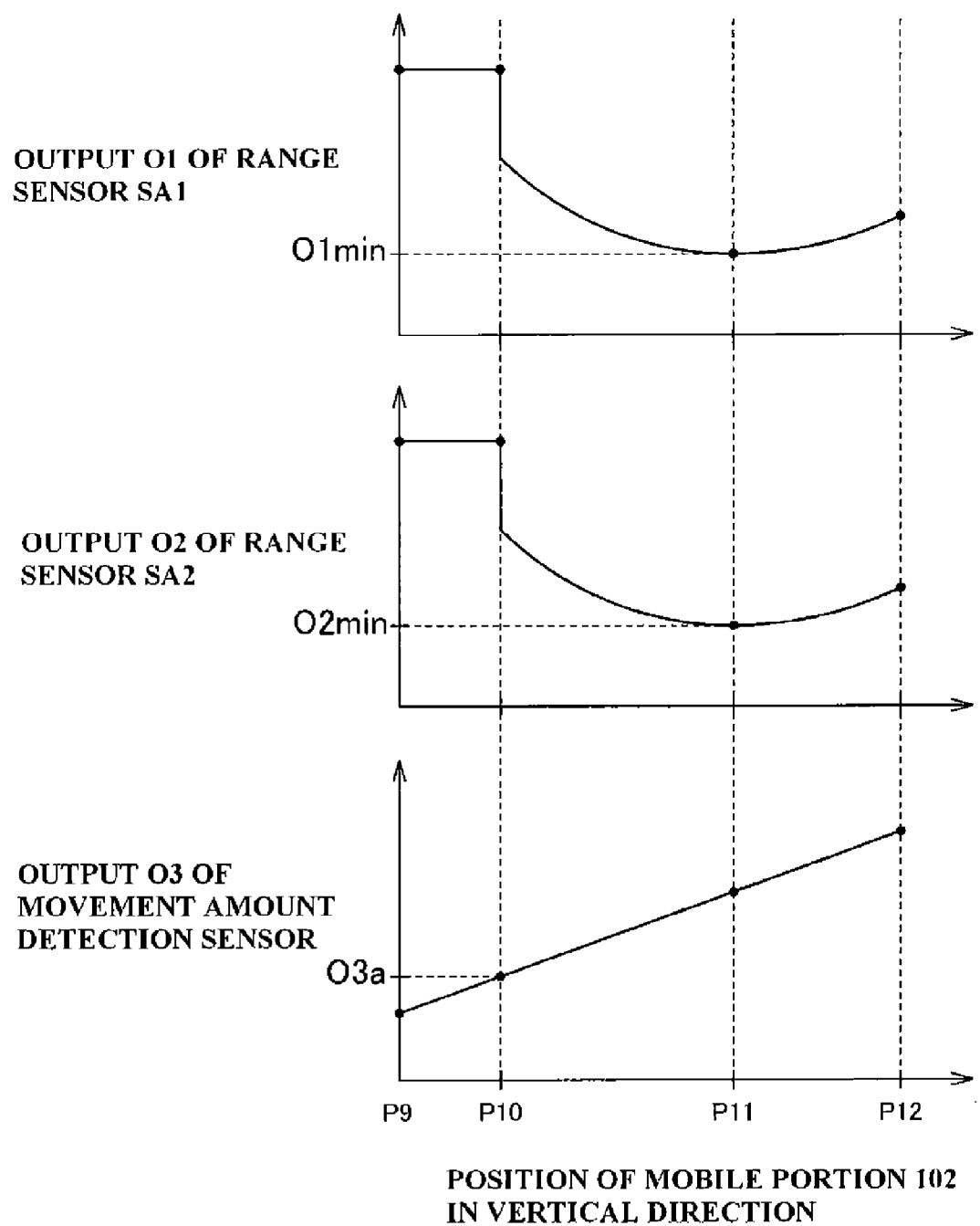
FIG. 13 is a diagram illustrating outputs of range sensors and a movement amount detection sensor provided in the body fat measurement device according to the first variation.

FIG. 9 is a schematic diagram illustrating the configuration of a trunk area dimension measurement unit in a body fat measurement device according to a first variation, and a method for measuring a trunk area width and a trunk area depth using the stated unit. FIGS. 10 through 12 are schematic diagrams illustrating a method for measuring a trunk area width and a trunk area depth using the trunk area dimension measurement unit in the body fat measurement device according to the present first variation. FIG. 13 is a diagram illustrating outputs of range sensors and a movement amount detection sensor provided in the body fat measurement device according to the first variation.

As shown in FIGS. 9 through 13, the body fat measurement device according to the present first variation differs from the body fat measurement device 1A according to the aforementioned first embodiment in terms of the configuration of the trunk area dimension measurement unit and the method for measuring the trunk area width and the trunk area depth using the trunk area dimension measurement unit.

Specifically, as shown in FIG. 9, compared to the trunk area dimension measurement unit 100A in the body fat measurement device 1A according to the aforementioned first embodiment, a trunk area dimension measurement unit 100B in the body fat measurement device according to the present first variation extends the range of movement of the mobile portion 102 upward, and when the mobile portion 102 is in the default position shown in FIG. 9, the range sensors SA1 and SA2 are disposed in a position that is higher than the trunk area 301 of the measurement subject 300.

FIGS. 9 through 12 are diagrams illustrating, in stages, a state in which the mobile portion 102 is moved downward (in the drawings, the direction of an arrow X1) in order to measure the trunk area dimensions. Here, FIG. 9 illustrates a state in which the mobile portion 102 is in the default position, and FIG. 10 illustrates a state in which the range sensors SA1 and SA2 are opposed to the top end of the trunk area 301 of the measurement subject 300 as a result of the mobile portion 102 being pushed downward. Meanwhile, FIG. 11 illustrates a state in which the range sensors SA1 and SA2 are opposed to the left and right ends of the trunk area 301 of the measurement subject 300 as a result of the mobile portion 102 being pushed downward, and FIG. 12 illustrates a state in which the mobile portion 102 has been pushed further downward and has reached a position in which the mobile portion 102 cannot move any further. Furthermore, FIG. 13 is a graph illustrating relationships between the position of the mobile portion 102 in the vertical direction and the output O1 of the range sensor SA1, the output O2 of the range sensor SA2, and the output O3 of the movement amount detection sensor; in FIG. 13, the positions of the mobile portion 102 illustrated in the aforementioned FIGS. 9 through 12 are respectively indicated as P9 through P12.

The trunk area width is calculated from the outputs O1 and O2 of the range sensors SA1 and SA2, outputted while the mobile portion 102 is moving. Note that the specific measurement method is the same as in the aforementioned first embodiment, and thus descriptions thereof will not be repeated here.

On the other hand, the trunk area depth is calculated from the outputs O1 and O2 of the range sensors SA1 and SA2 outputted while the mobile portion 102 is moving and the output O3 of the movement amount detection sensor, outputted while the mobile portion 102 is moving. As shown in FIG. 10, the mobile portion 102 passes through the height at which the top end of the trunk area 301 of the measurement subject 300 is located by being pushed downward, and thus characteristic points such as those shown in FIG. 13 (and specifically, points where the outputs O1 and O2 drop drastically) appear in the outputs O1 and O2 of the range sensors SA1 and SA2 at that time.

Accordingly, as shown in FIG. 10, the trunk area depth 2×b of the measurement subject 300 is calculated based on the following Formula (9) using B2, which is a distance based on an output O3a of the movement amount detection sensor at the stated characteristic points (see FIG. 13) appearing in the outputs of the range sensors SA1 and SA2 while the mobile portion 102 is moving, and a predetermined distance B (that is, a distance between the range sensors SA1 and SA2 and the top surface of the mat 121 in the back area electrode support unit 120 when the mobile portion 102 is in the default position; see also FIG. 10).

$$2 \times b = B - B2 \qquad \text{Formula (9)}$$

In this manner, like the body fat measurement device 1A according to the aforementioned first embodiment, the body fat measurement device according to the present first variation is configured so that the trunk area width and the trunk area depth can be measured by the two range sensors SA1 and SA2 and the one movement amount detection sensor provided in the trunk area dimension measurement unit 100B. To be more specific, in the body fat measurement device according to the present first variation, the mobile portion 102 is attached to the base portions 101 so that the mobile portion 102 is capable of moving along the trunk area depth direction, the trunk area width detection unit 24A is configured of the stated two range sensors SA1 and SA2 provided in predetermined positions on the mobile portion 102, the trunk area depth detection unit 24B is configured of the stated two range sensors SA1 and SA2 provided in predetermined positions on the mobile portion 102 and the stated one movement amount detection sensor that detects the amount by which the mobile portion 102 has moved, and as a result, the trunk area width and the trunk area depth can be measured.

Therefore, employing the stated configuration achieves the same effects as the effects of the aforementioned first embodiment. In the body fat measurement device 1A according to the aforementioned first embodiment, the configuration is such that the trunk area depth is measured by the upper frame portion 111 of the trunk area dimension measurement unit 100A making contact with the trunk area 301 of the measurement subject 300; however, in the body fat measurement device according to the present first variation, if the configuration is such that the upper frame portion 111 is stopped before making contact with the top surface of the trunk area 301 of the measurement subject 300 using a stopper or the like, the trunk area depth is measured without the upper frame portion 111 of the trunk area dimension measurement unit 100B making contact with the top surface of the trunk area 301 of the measurement subject 300. Accordingly, using such a configuration eliminates a sense of pressure on the measurement subject resulting from the trunk area dimension measurement unit making contact with the trunk area, making it possible to further reduce the burden on the measurement subject.

Second Variation

Figure 14:
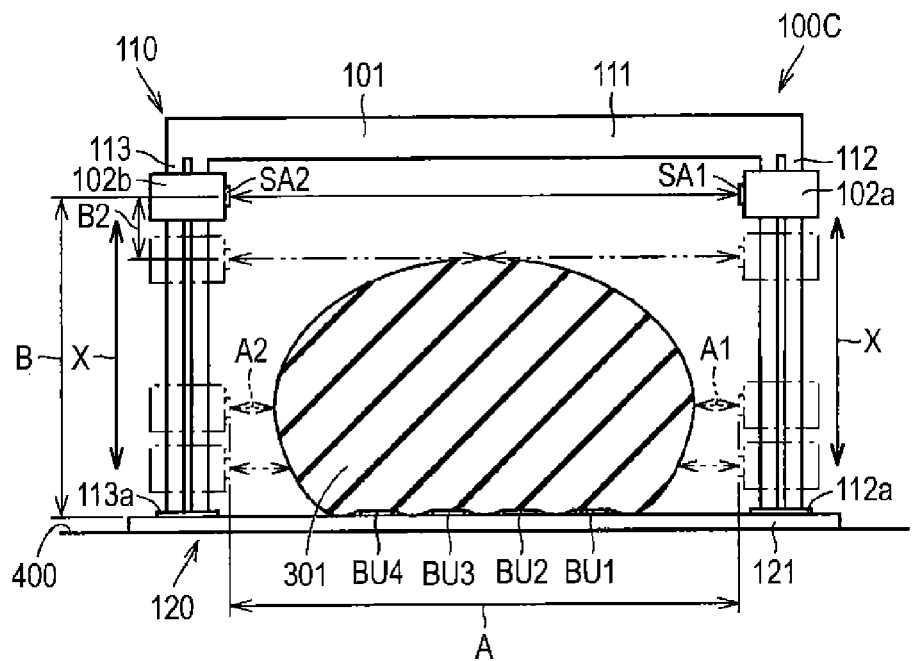
FIG. 14 is a schematic diagram illustrating the configuration of a trunk area dimension measurement unit in a body fat measurement device according to a second variation, and a method for measuring a trunk area width and a trunk area depth using the stated unit.

FIG. 14 is a schematic diagram illustrating the configuration of a trunk area dimension measurement unit in a body fat measurement device according to a second variation, and a method for measuring a trunk area width and a trunk area depth using the stated unit. Next, the configuration of the trunk area dimension measurement unit in the body fat measurement device according to the present second variation, and a method for measuring a trunk area width and a trunk area depth using the stated unit, will be described with reference to FIG. 14. Note that in FIG. 14, solid lines indicate a state in which mobile portions 102a and 102b (mentioned later) are in default positions, whereas broken lines indicate a state in which the mobile portions 102a and 102b have moved from the default positions.

As shown in FIG. 14, the body fat measurement device according to the present second variation differs from the body fat measurement device according to the aforementioned first variation in terms of the configuration of the trunk area dimension measurement unit.

Specifically, in a trunk area dimension measurement unit 100C in the body fat measurement device according to the present second variation, the base portion 101 is configured as the entire frame member 110 that is in turn configured of the upper frame portion 111, the right side frame portion 112, and the left side frame portion 113; of these, the mobile portion 102a is attached to the right side frame portion 112 in a mobile state, whereas the mobile portion 102b is attached to the left side frame portion 113 in a mobile state. More specifically, the mobile portions 102a and 102b are engaged with respective guide rails that are erected along the right side frame portion 112 and the left side frame portion 113 in the vertical direction, and move along the guide rails in the trunk area depth direction (the direction indicated by the arrows X in FIG. 14) as a result of being driven by a driving means such as a motor or the like (not shown). Here, the range sensors SA1 and SA2 are provided on the inner side surfaces of the mobile portions 102a and 102b, respectively.

In addition, a movement amount detection sensor (not shown) for detecting amounts by which the mobile portions 102a and 102b move from the default positions indicated by the solid lines in FIG. 14 is provided in the trunk area dimension measurement unit 100C. Here, if the configuration is such that the mobile portions 102a and 102b move simultaneously using a linking mechanism or the like, it is not necessary to provide multiple individual movement amount detection sensors, and the amount by which the mobile portions 102a and 102b move can be detected using a single movement amount detection sensor.

The trunk area width is calculated from the outputs O1 and O2 of the range sensors SA1 and SA2, outputted while the mobile portions 102a and 102b are moving. Note that the specific measurement method is the same as in the aforementioned first embodiment, and thus descriptions thereof will not be repeated here.

On the other hand, the trunk area depth is calculated from the outputs O1 and O2 of the range sensors SA1 and SA2 outputted while the mobile portions 102a and 102b are moving and the output O3 of the movement amount detection sensor outputted while the mobile portions 102a and 102b are moving. Note that the specific measurement method is the same as that in the aforementioned first variation, and thus descriptions thereof will not be repeated here.

In this manner, like the body fat measurement device according to the aforementioned first variation, the body fat measurement device according to the present second variation is configured so that the trunk area width and the trunk area depth can be measured by the two range sensors SA1 and SA2 and the one movement amount detection sensor provided in the trunk area dimension measurement unit 100C. To be more specific, in the body fat measurement device according to the present second variation, the mobile portions 102 are attached to the base portion 101 so that the mobile portions 102 are capable of moving along the trunk area depth direction, the trunk area width detection unit 24A is configured of the stated two range sensors SA1 and SA2 provided in predetermined positions on the mobile portions 102, the trunk area depth detection unit 24B is configured of the stated two range sensors SA1 and SA2 provided in predetermined positions on the mobile portions 102 and the stated one movement amount detection sensor that detects the amount by which the mobile portions 102 have moved, and as a result, the trunk area width and the trunk area depth can be measured.

Therefore, employing the stated configuration achieves the same effects as the effects of the aforementioned first variation. Here, although the body fat measurement device according to the aforementioned first variation is configured so that the mobile portion moves as a result of the measurement subject or an assistant pushing the mobile portion downward, the body fat measurement device according to the present second variation is configured so that the mobile portion is moved by a driving means such as a motor. Accordingly, employing such a configuration further simplifies the operations performed during measurement, making it possible to realize a highly-usable body fat measurement device.

Third Variation

Figure 15:
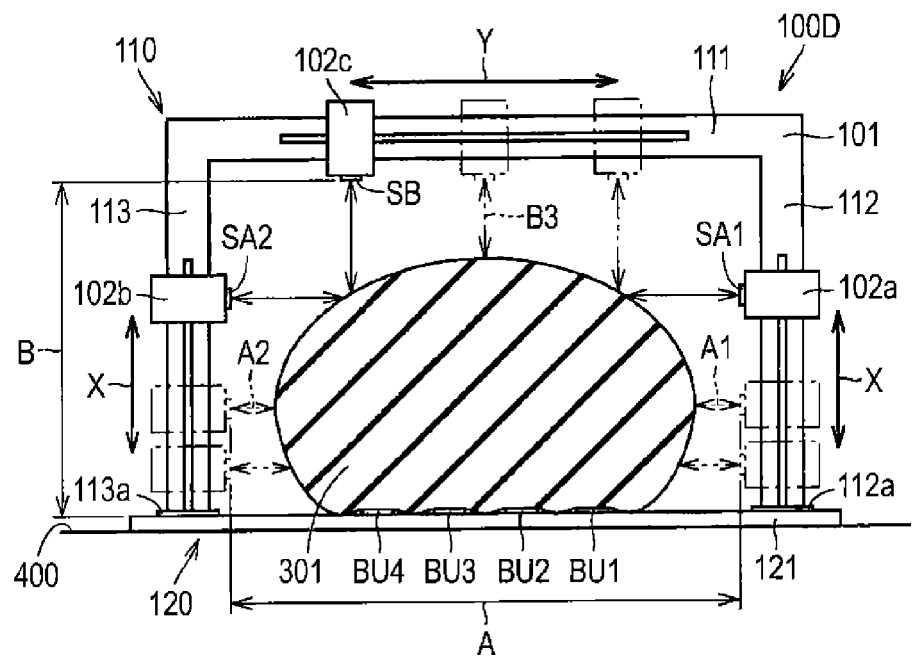
FIG. 15 is a schematic diagram illustrating the configuration of a trunk area dimension measurement unit in a body fat measurement device according to a third variation, and a method for measuring a trunk area width and a trunk area depth using the stated unit.
Figure 16:
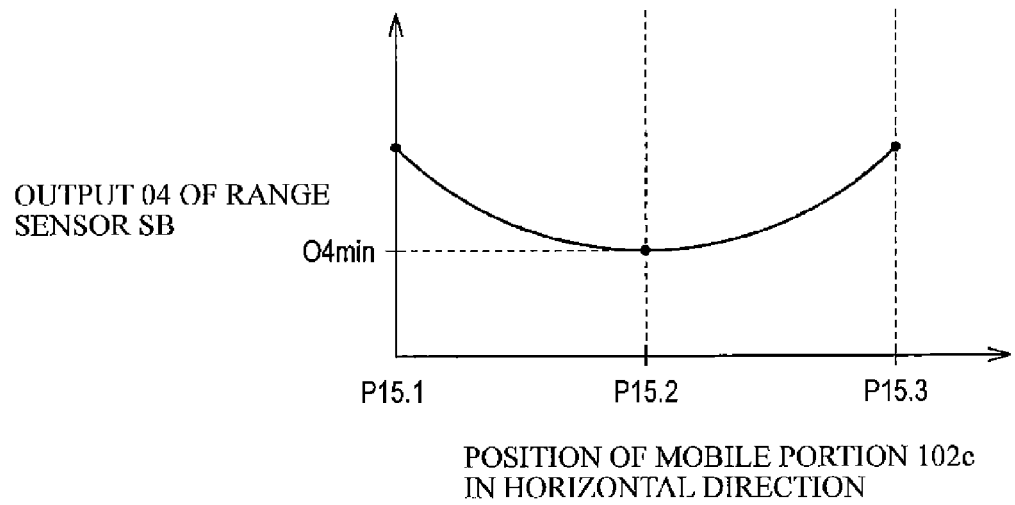
FIG. 16 is a diagram illustrating an output of a range sensor provided in the body fat measurement device according to the third variation.

FIG. 15 is a schematic diagram illustrating the configuration of a trunk area dimension measurement unit in a body fat measurement device according to a third variation, and a method for measuring a trunk area width and a trunk area depth using the stated unit. FIG. 16 is a diagram illustrating outputs of range sensors provided in the body fat measurement device according to the present third variation. Next, the configuration of the trunk area dimension measurement unit in the body fat measurement device according to the present third variation, and a method for measuring a trunk area width and a trunk area depth using the stated unit, will be described with reference to FIGS. 15 and 16. Note that in FIG. 15, solid lines indicate a state in which mobile portions 102*a* through 102*c* (mentioned later) are in default positions, whereas broken lines indicate a state in which the mobile portions 102*a* through 102*c* have moved from the default positions. FIG. 16, meanwhile, is a graph illustrating a relationship between the position of the mobile portion 102*c* in the horizontal direction and an output O4 of a range sensor SB (mentioned later), and in FIG. 16, the positions of the mobile portion 102*c* indicated in the aforementioned FIG. 15 are indicated by P15.1 through P15.3, respectively.

As shown in FIG. 15, the body fat measurement device according to the present third variation differs from the body fat measurement device according to the aforementioned second variation in terms of the configuration of the trunk area dimension measurement unit and the method for measuring the trunk area width and the trunk area depth using the trunk area dimension measurement unit.

Specifically, as shown in FIG. 15, a trunk area dimension measurement unit 100D of the body fat measurement device according to the present third variation includes the mobile portion 102*c* attached in a mobile state to the upper frame portion 111 serving as the base portion 101, in addition to the mobile portions 102*a* and 102*b* attached in a mobile state to the right side frame portion 112 and the left side frame portion 113 serving as the base portion 101. To be even more specific, the mobile portion 102*c* is engaged with a guide rail that is erected along the upper frame portion 111 in the horizontal direction, and moves along the guide rail in the trunk area width direction (the direction indicated by the arrow Y in FIG. 15) as a result of being driven by a driving means such as a motor or the like (not shown). Here, the range sensor SB is provided on the inner side surface of the mobile portion 102*c*. Note that in the body fat measurement device according to the present third variation, the trunk area dimension measurement unit 100D is not provided with a movement amount detection sensor.

Meanwhile, compared to the trunk area dimension measurement unit 100C of the body fat measurement device according to the second variation, the range of movement of the mobile portions 102*a* and 102*b* is reduced in the downward direction in the trunk area dimension measurement unit 100D of the body fat measurement device according to the present third variation; when the mobile portions 102*a* and 102*b* are in the default positions indicated by the solid lines, the range sensors SA1 and SA2 are disposed to the sides of the trunk area 301 of the measurement subject 300.

The trunk area width is calculated from the outputs O1 and O2 of the range sensors SA1 and SA2, outputted while the mobile portions 102*a* and 102*b* are moving. Note that the specific measurement method is the same as in the aforementioned first embodiment, and thus descriptions thereof will not be repeated here.

On the other hand, the trunk area depth is calculated from the output O3 of the range sensor SB, outputted while the mobile portion 102*c* is moving. As shown in FIG. 15, when the range sensor SB is located above the trunk area 301 of the measurement subject 300, the light emitted from the range sensor SB falls onto the top surface of the trunk area 301 of the measurement subject 300 (that is, the surface of the abdominal area). For this reason, as shown in FIG. 16, the output O3 outputted from the range sensor SB while the mobile portion 102*c* is moving is an output that is based on the distance from the range sensor SB to the trunk area 301 of the measurement subject 300 in the vertical direction.

Accordingly, as shown in FIG. 15, the trunk area depth 2×b of the measurement subject 300 is calculated based on the following Formula (10) using a distance B3, which is a distance based on a minimum value O3min (see FIG. 16) of the output of the range sensor SB (that is, the distance between the range sensor SB and the upper end of the trunk area 301 of the measurement subject 300), and a predetermined distance B (that is, a distance between the range sensor SB and the top surface of the mat 121 in the back area electrode support unit 120).

$$2 \times b = B - B3 \qquad \text{Formula (10)}$$

In this manner, the body fat measurement device according to the present third variation is configured so that the trunk area width and the trunk area depth can be measured by the three range sensors SA1, SA2, and SB provided in the trunk area dimension measurement unit 100D. To be more specific, in the body fat measurement device according to the present third variation, the mobile portions 102*a* and 102*b* are attached to the base portion 101 so that the mobile portions 102*a* and 102*b* can move along the trunk area depth direction, the mobile portion 102*c* is attached to the base portion 101 so that the mobile portion 102*c* can move along the trunk area width direction, the trunk area width detection unit 24A is configured of the stated two range sensors SA1 and SA2 provided in predetermined positions on the mobile portions 102*a* and 102*b*, respectively, and the trunk area depth detection unit 24B is configured of the stated range sensor SB provided in a predetermined position on the mobile portion 102*c*; as a result, the trunk area width and the trunk area depth can be measured.

Accordingly, by employing such a configuration, the trunk area width and trunk area depth can be measured with certainty and accurately without using many sensors; as a result, it is possible to realize a body fat measurement device that is capable of accurately measuring body fat masses such as visceral fat mass and that is easy to operate and use when taking such measurements, and that can be manufactured for a low cost. Moreover, by employing the aforementioned configuration, it is possible for the measurement subject to take measurements by him/herself without help from an assistant or the like, which makes it possible to realize a body fat measurement device that is suited to taking daily measurements of visceral fat masses or the like.

In addition, although the body fat measurement device 1A according to the stated first embodiment and the body fat measurement device according to the stated first and second variations require the movement amount detection sensor in addition to the range sensor in order to detect the trunk area dimensions, the body fat measurement device according to the present third variation can accurately measure the trunk area width and the trunk area depth using only range sensors and without using a movement amount detection sensor, making it possible to simplify the device configuration.

Fourth Variation

Figure 17:
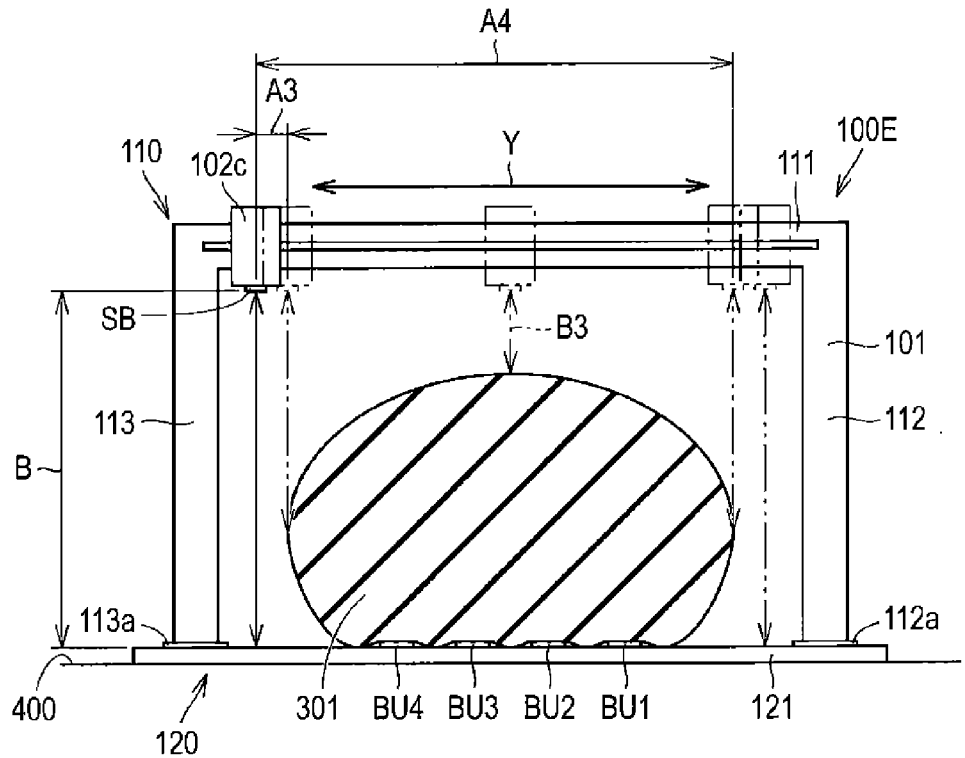
FIG. 17 is a schematic diagram illustrating the configuration of a trunk area dimension measurement unit in a body fat measurement device according to a fourth variation, and a method for measuring a trunk area width and a trunk area depth using the stated unit.
Figure 18:
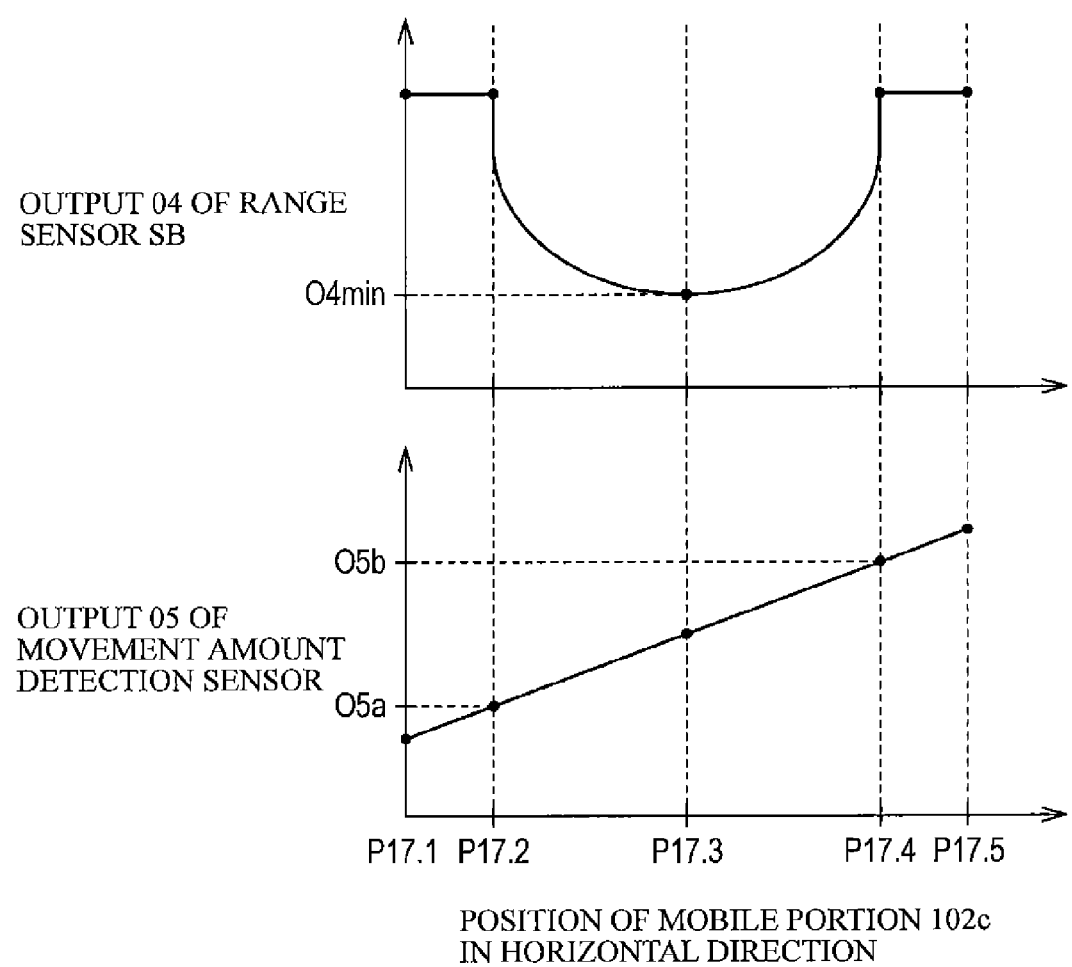
FIG. 18 is a diagram illustrating outputs of range sensors and a movement amount detection sensor provided in the body fat measurement device according to the fourth variation.

FIG. 17 is a schematic diagram illustrating the configuration of a trunk area dimension measurement unit in a body fat measurement device according to a fourth variation, and a method for measuring a trunk area width and a trunk area depth using the stated unit. FIG. 18 is a diagram illustrating outputs of range sensors provided in the body fat measurement device according to the present fourth variation. Next, the configuration of the trunk area dimension measurement unit in the body fat measurement device according to the present fourth variation, and a method for measuring a trunk area width and a trunk area depth using the stated unit, will be described with reference to FIGS. 17 and 18. Note that in FIG. 17, solid lines indicate a state in which the mobile portion 102c (mentioned later) is in a default position, whereas broken lines indicate a state in which the mobile portion 102c has moved from the default position. FIG. 18, meanwhile, is a graph illustrating a relationship between the position of the mobile portion 102c in the horizontal direction and the output O4 of the range sensor SB and an output O5 of a movement amount detection sensor (mentioned later), and in FIG. 18, the positions of the mobile portion 102c indicated in the aforementioned FIG. 17 are indicated by P17.1 through P17.5, respectively.

As shown in FIG. 17, the body fat measurement device according to the present fourth variation differs from the body fat measurement device according to the aforementioned third variation in terms of the configuration of the trunk area dimension measurement unit and the method for measuring the trunk area width and the trunk area depth using the trunk area dimension measurement unit.

Specifically, as shown in FIG. 17, in a trunk area dimension measurement unit 100E of the body fat measurement device according to the present fourth variation, mobile portions are not attached to the right side frame portion 112 and the left side frame portion 113 that serve as the base portions 101, and the mobile portion 102c is attached only to the upper frame portion 111 that serves as the base portion 101; the range sensor SB is provided in a predetermined position on the mobile portion 102c. Instead, a movement amount detection sensor (not shown) for detecting amounts by which the mobile portion 102c moves from the default positions indicated by the solid lines in FIG. 17 is provided in the trunk area dimension measurement unit 100E of the body fat measurement device according to the present fourth variation. Meanwhile, the range sensor SB is disposed in a location that is distanced from the trunk area 301 of the measurement subject 300 in the horizontal direction when the mobile portion 102c is in the default position indicated by the solid lines.

The trunk area width is calculated from the output O4 of the range sensor SB outputted while the mobile portion 102c is moving and the output O5 of the movement amount detection sensor outputted while the mobile portion 102c is moving. As shown in FIG. 17, the mobile portion 102c passes through positions corresponding to the left and right ends of the trunk area 301 of the measurement subject 300 by moving along the horizontal direction, and thus characteristic points such as those shown in FIG. 18 (and specifically, points where the output O4 drops or rises drastically) appear in the output O4 of the range sensor SB at that time.

Accordingly, as shown in FIG. 17, a trunk area width 2×a of the measurement subject 300 is calculated based on the following Formula (11) using distances A3 and A4 that are distances based on outputs O5a and O5b of the movement amount detection sensor at the stated characteristic points (see FIG. 18) appearing in the outputs of the range sensors SA1 and SA2 while the mobile portion 102 is moving (A3: the distance between the position of the range sensor SB when the mobile portion 102c is in the default position and the left end of the trunk area 301 of the measurement subject 300; A4: the distance between the position of the range sensor SB when the mobile portion 102c is in the default position and the right end of the trunk area 301 of the measurement subject 300).

$$2 \times a = A4 - A3 \quad \text{Formula (11)}$$

On the other hand, the trunk area depth is calculated from the output O4 of the range sensor SB, outputted while the mobile portion 102c is moving. Note that the specific measurement method is the same as that in the aforementioned third variation, and thus descriptions thereof will not be repeated here.

In this manner, the body fat measurement device according to the present fourth variation is configured so that the trunk area width and the trunk area depth can be measured by the one range sensor SB provided in the trunk area dimension measurement unit 100E and the one movement amount detection sensor provided in the trunk area dimension measurement unit 100E. More specifically, in the body fat measurement device according to the present fourth variation, the mobile portion 102c is attached to the base portion 101 so that the mobile portion 102c can move in the trunk area width direction, and the trunk area width detection unit 24A and the trunk area depth detection unit 24B are configured using the stated one range sensor SB provided in the predetermined position on the mobile portion 102c and the stated one movement amount detection sensor that detects the amount by which the mobile portion 102c moves; as a result, the trunk area width and the trunk area depth can be measured.

Accordingly, by employing such a configuration, the trunk area width and trunk area depth can be measured with certainty and accurately without using many sensors; as a result, it is possible to realize a body fat measurement device that is capable of accurately measuring body fat masses such as visceral fat mass and that is easy to operate and use when taking such measurements, and that can be manufactured for a low cost. Moreover, by employing the aforementioned configuration, it is possible for the measurement subject to take measurements by him/herself without help from an assistant or the like, which makes it possible to realize a body fat measurement device that is suited to taking daily measurements of visceral fat masses or the like.

Furthermore, the body fat measurement device 1A according to the aforementioned first embodiment and the body fat measurement devices according to the first through third variations require a total of at least three sensors in order to detect the trunk area width and the trunk area depth; however, in the body fat measurement device according to the present fourth variation, the trunk area width and trunk area depth can be measured with a high degree of accuracy using a total of only two sensors, making it possible to further simplify the device configuration.

Second Embodiment

Figure 19:
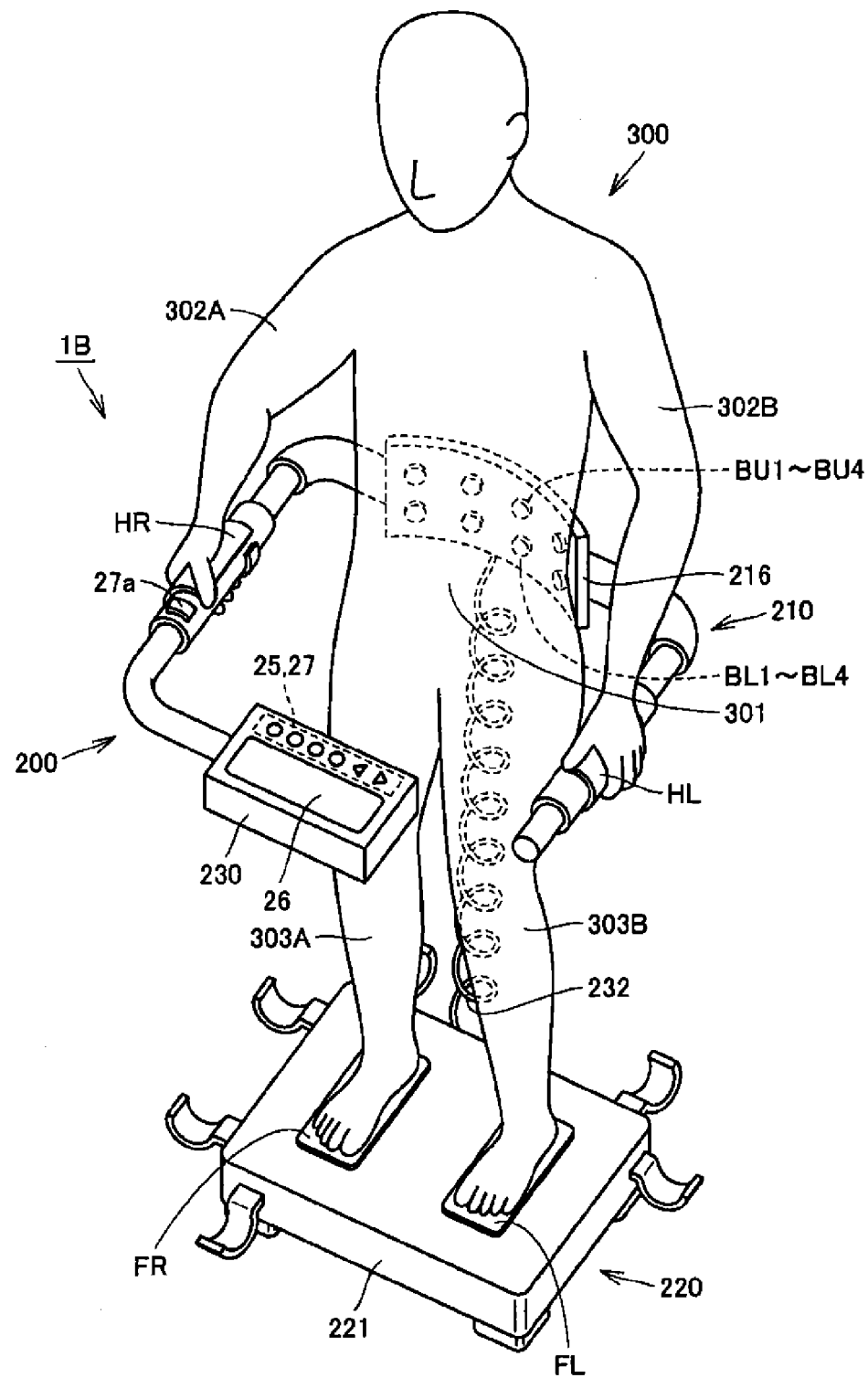
FIG. 19 is a perspective view illustrating the configuration of a body fat measurement device and a measurement position according to a second embodiment of the present invention.
Figure 20:
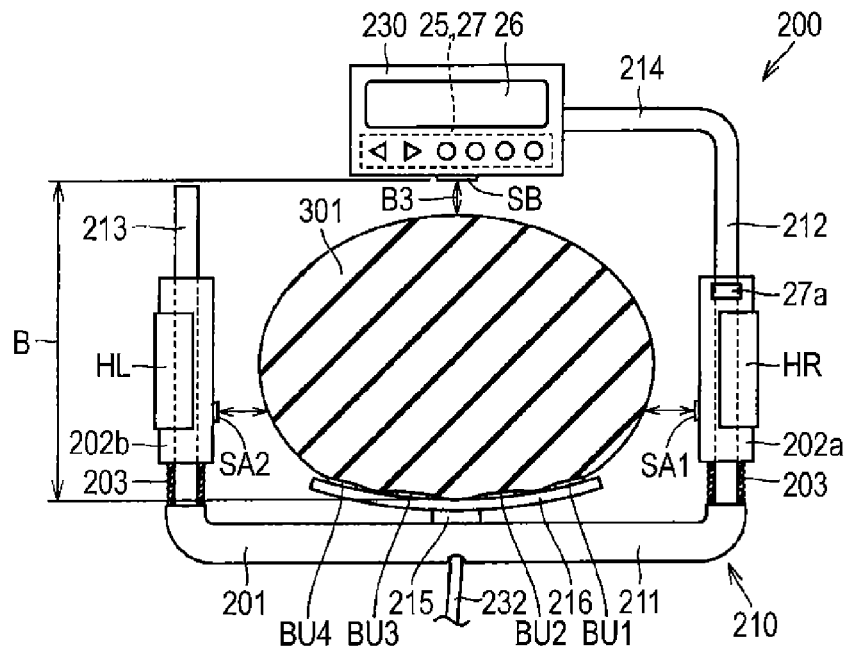
FIG. 20 is a schematic diagram illustrating the configuration of a trunk area dimension measurement unit in the body fat measurement device according to the second embodiment of the present invention, and a method for measuring a trunk area width and a trunk area depth using the stated unit.
Figure 21:
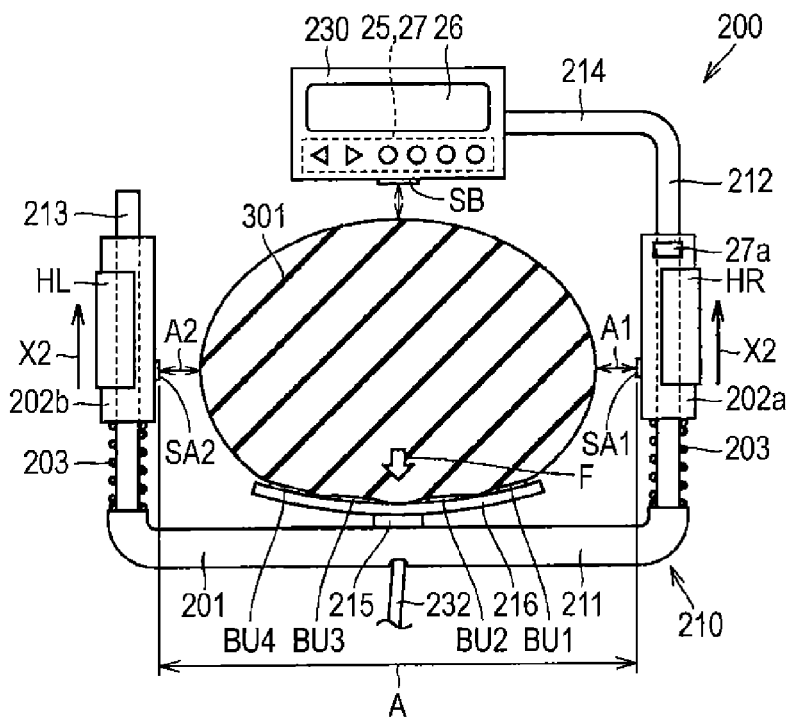
FIG. 21 is a schematic diagram illustrating a method for measuring a trunk area width and a trunk area depth using the trunk area dimension measurement unit in the body fat measurement device according to the second embodiment of the present invention.
Figure 22:
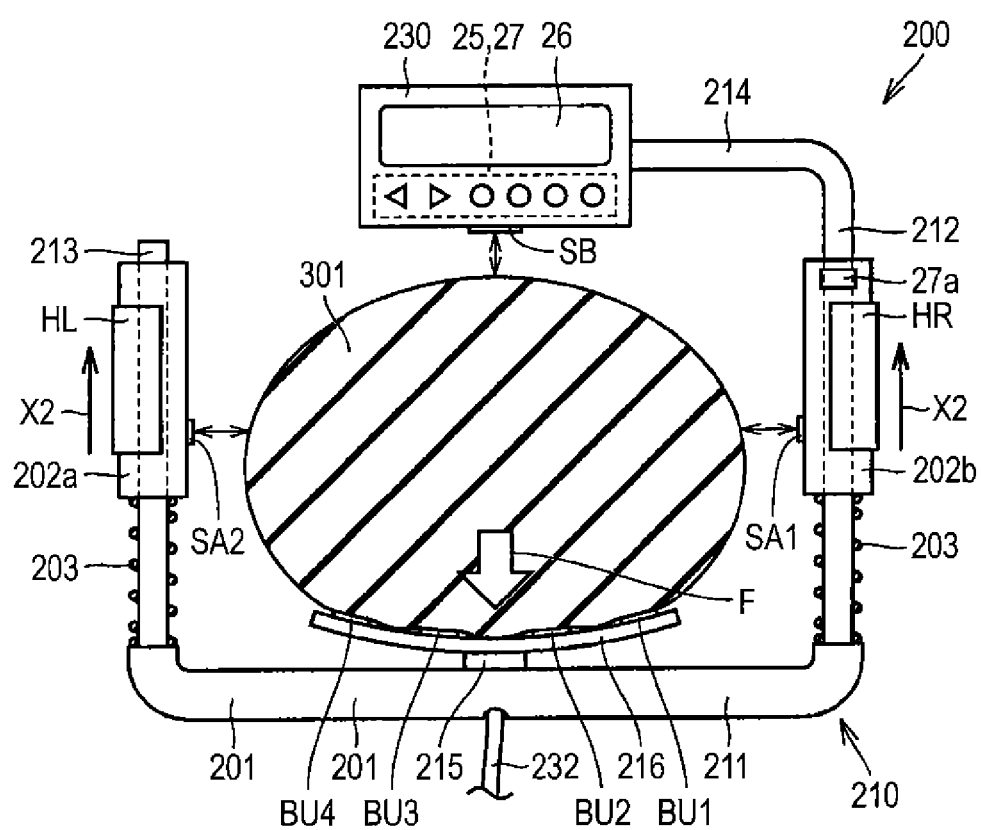
FIG. 22 is a schematic diagram illustrating a method for measuring a trunk area width and a trunk area depth using the trunk area dimension measurement unit in the body fat measurement device according to the second embodiment of the present invention.

FIG. 19 is a perspective view illustrating the configuration of a body fat measurement device and a measurement position according to a second embodiment of the present invention. FIG. 20 is a schematic diagram illustrating the configuration of a trunk area dimension measurement unit in the body fat measurement device according to the present embodiment, and a method for measuring a trunk area width and a trunk area depth using the stated unit. FIGS. 21 and 22, meanwhile, are schematic diagrams illustrating a method for measuring the trunk area width and the trunk area depth using the trunk area dimension measurement unit in the body fat measurement device according to the present embodiment. The configuration of the body fat measurement device according to the present embodiment, the measurement position, the configuration of the trunk area dimension measurement unit, a method for measuring the trunk area width and the trunk area depth using the stated device/unit, and so on will be described with reference to FIGS. 19 through 22.

First, the configuration of the body fat measurement device and the configuration of the trunk area dimension measurement unit according to the present embodiment will be described with reference to FIGS. 19 and 20.

As shown in FIG. 19, a body fat measurement device 1B according to the present embodiment primarily includes a trunk area dimension measurement unit 200 that also functions as a fitting unit for fitting the arm electrodes HR and HL and the back area electrodes BU1-BU4 and BL1-BL4 to the measurement subject 300, and a platform unit 220 for fitting the leg electrodes FR and FL to the measurement subject 300. The various functional blocks shown in FIG. 2 are provided in the trunk area dimension measurement unit 200 and the platform unit 220. The trunk area dimension measurement unit 200 and the platform unit 220 are electrically connected by a connection cable 232, and some of the signal exchanges between the various functional blocks illustrated in FIG. 2 are carried out via the connection cable 232.

As shown in FIGS. 19 and 20, the trunk area dimension measurement unit 200 is configured of a unit having a frame shape that can be disposed so as to surround the trunk area 301 of the measurement subject 300, who is standing, by the measurement subject 300 entering thereinto (that is, by inserting the trunk area 301 thereinto). More specifically, the trunk area dimension measurement unit 200 is configured of a frame member 210 that includes a bar-shaped rear frame portion 211, a bar-shaped right-side frame portion 212, a bar-shaped left-side frame portion 213, and a bar-shaped front frame portion 214, and includes: a base portion 201 whose position relative to the trunk area 301 of the measurement subject 300 does not change when the unit is disposed surrounding the trunk area 301 of the measurement subject 300; and a pair of mobile portions 202a and 202b attached in a mobile state to the stated base portion 201 so that the position of the mobile portions 202a and 202b relative to the trunk area 301 of the measurement subject 300 can change when the unit is disposed surrounding the trunk area 301 of the measurement subject 300.

The base portion 201 is configured as the entire frame member 210. On the other hand, the pair of mobile portions 202a and 202b are attached to the right-side frame portion 212 and the left-side frame portion 213, respectively, and are configured to be capable of moving along the depth direction, which is the direction in which the right-side frame portion 212 and the left-side frame portion 213 extend (that is, the trunk area depth direction).

Elastic members 203 (not shown in FIG. 19; see FIG. 20) configured of springs or the like and serving as biasing members are provided and held on the outsides of the right-side frame portion 212 and the left-side frame portion 213 to which the mobile portions 202a and 202b are respectively attached. The elastic members 203 are members for biasing the mobile portions 202a and 202b rearward, and in the case where the mobile portions 202a and 202b have been pushed forward from the default positions shown in FIG. 20, are for returning the mobile portions 202a and 202b to the default positions by pushing the mobile portions 202a and 202b rearward.

An electrode support member 216 is disposed in approximately the center of the rear frame portion 211 of the frame member 210 so as to protrude inward. The electrode support member 216 is configured of a curved plate that is bent so that both ends thereof are positioned forward and the center thereof is positioned rearward. The aforementioned back area electrodes BU1-BU4 and BL1-BL4 shown in FIG. 2 are arranged in rows and columns on the front surface of the electrode support member 216. The back area electrodes BU1-BU4 and BL1-BL4 are provided protruding slightly from the front surface of the electrode support member 216 so as to make contact with the back area surface of the trunk area 301 of the measurement subject 300, who is standing, with certainty when the electrode support member 216 is pressed against the back area surface.

Meanwhile, the electrode support member 216 is attached to the rear frame portion 211 of the frame member 210 via a connection portion 215 including, for example, a ball joint. Through this, the electrode support member 216 is supported by the rear frame portion 211 so as to be capable of swinging. Note that it is preferable for the direction of the swinging to be limited so that the electrode support member 216 can swing only to the left and right in the horizontal plane. By employing such a configuration, during a fitted state (mentioned later), the back area electrodes BU1-BU4 and BL1-BL4 provided on the front surface of the electrode support member 216 can be brought into contact with the back area surface of the trunk area 301 of the measurement subject 300 with certainty and with an appropriate pressure and in an appropriate direction.

The arm electrode HR shown in FIG. 2 is provided on the mobile portion 202a attached to the right-side frame portion 212 of the frame member 210. The arm electrode FIR is exposed on the surface of the mobile portion 202a, and preferably, is disposed so that the surface of the arm electrode HR that makes contact with the palm of the right hand of the measurement subject 300 primarily faces outward from the frame member 210.

Meanwhile, a measure button 27a is provided on the mobile portion 202a attached to the right-side frame portion 212 of the frame member 210. Preferably, the measure button 27a is provided in a location adjacent to the arm electrode HR. As a result, it is not necessary for the measurement subject 300 to move his/her right arm 302A during measurement, which makes it possible to provide superior operability.

The arm electrode HL shown in FIG. 2 is provided on the mobile portion 202b attached to the left-side frame portion 213 of the frame member 210. The arm electrode HL is exposed on the surface of the mobile portion 202b, and preferably, is disposed so that the surface of the arm electrode HL that makes contact with the palm of the left hand of the measurement subject 300 primarily faces outward from the frame member 210.

A display unit portion 230 is attached to the front frame portion 214 of the frame member 210. The display unit 26 is provided on the top surface of the display unit portion 230, and furthermore, the operating unit 27, excluding the measurement subject information input unit 25 and the measure button 27a, is provided on an area of the top surface of the display unit portion 230 that is adjacent to the display unit 26. Note that it is preferable for the display unit portion 230 to be located in front of the measurement subject 300 during the fitted state, and for this reason, the display unit portion 230 is disposed forward from the aforementioned electrode support member 216.

As shown in FIG. 20, the range sensors SA1 and SA2, serving as the trunk area width detection unit 24A shown in FIG. 2, are attached to the inner surfaces of the pair of mobile portions 202a and 202b attached to the right-side frame portion 212 and the left-side frame portion 213 of the trunk area dimension measurement unit 200 (that is, the surfaces of the trunk area dimension measurement unit 200 that face the trunk area 301 of the measurement subject 300 when the trunk area dimension measurement unit 200 is disposed surrounding the trunk area 301 of the measurement subject 300). Both of the range sensors SA1 and SA2 emit light toward the inner side of the trunk area dimension measurement unit 200 along the horizontal direction, and measure distances from the range sensors SA1 and SA2 to the trunk area 301 of the measurement subject 300, which is the area to be detected, by receiving light reflected therefrom.

The range sensors SA1 and SA2 move in the depth direction along with the mobile portions 202a and 202b when the mobile portions 202a and 202b move in the depth direction. Here, the range sensors SA1 and SA2 are disposed in positions on the sides of the trunk area 301 of the measurement subject 300 when the mobile portions 202a and 202b are in the default positions shown in FIG. 20.

Furthermore, as shown in FIG. 20, the range sensor SB, serving as the trunk area depth detection unit 24B shown in FIG. 2, is attached to the inner side surface of the display unit portion 230. The range sensor SB emits light toward the inner side of the trunk area dimension measurement unit 200 along the horizontal direction, and measures the distance from the range sensor SB to the trunk area 301 of the measurement subject 300, which is the area to be detected, by receiving light reflected therefrom.

Meanwhile, as shown in FIG. 19, the platform unit 220 has a box shape, and includes a platform portion 221 having a top surface onto which the measurement subject 300 steps. The leg electrodes FR and FL shown in FIG. 2 are provided in predetermined positions of the top surface of the platform portion 221. The leg electrodes FR and FL are positioned so as to be exposed on the top surface of the platform portion 221. Here, the configuration is such that the contact surfaces of the leg electrodes FR and FL that make contact with the sole of the measurement subject's right foot and the sole of the measurement subject's left foot are both facing upward.

The aforementioned control unit 10, constant current generation unit 21, terminal switching unit 22, potential difference detection unit 23, memory unit 29, and so on shown in FIG. 2 may be provided within the trunk area dimension measurement unit 200, or may be provided within the platform unit 220. Furthermore, although the measurement subject information input unit 25, the display unit 26, and operating unit 27 are provided in the trunk area dimension measurement unit 200 of the body fat measurement device 1B according to the present embodiment, those units may be provided within the platform unit 220.

Next, a measurement position to be assumed by the measurement subject when measuring a body fat mass such as a visceral fat mass using the body fat measurement device according to the present embodiment will be described with reference to FIG. 19.

As shown in FIG. 19, during measurement, the measurement subject 300 first steps onto the platform unit 220 while standing erect, and then holds the trunk area dimension measurement unit 200 and inserts the trunk area 301 thereinto. At this time, the sole of the foot on the right leg 303A makes contact with the leg electrode FR provided in the platform unit 220, and the sole of the foot on the left leg 303B makes contact with the leg electrode FL provided in the platform unit 220; meanwhile, the palms of the hand of the right arm 302A makes contact with the arm electrode HR provided on the mobile portion 202a of the trunk area dimension measurement unit 200, and the palm of the hand of the left arm 302B makes contact with the arm electrode HL provided on the mobile portion 202b of the trunk area dimension measurement unit 200.

After this, the measurement subject 300 adjusts the position of the trunk area dimension measurement unit 200 so that the trunk area dimension measurement unit 200 is at a height corresponding to the location of the navel and so that the body axis is located in the center of the trunk area dimension measurement unit 200, and then pushes the trunk area dimension measurement unit 200 forward while maintaining the horizontal orientation thereof. As a result, the electrode support member 216 provided in the trunk area dimension measurement unit 200 is pushed against the back area of the measurement subject 300 and the back area electrodes BU1-BU4 and BL1-BL4 provided in the electrode support member 216 are pressed against the back area surface of the trunk area 301 of the measurement subject 300, and the mobile portions 202a and 202b move forward along the right-side frame portion 212 and the left-side frame portion 213 that serve as the base portion 201; at this time, the trunk area depth and trunk area width are measured using the trunk area dimension measurement unit 200.

After this, the measurement subject 300 presses the measure button 27a with the thumb of the hand of the right arm 302A while maintaining the stated position, and as a result, the body impedance is measured using the electrodes HR, HL, BU1-BU4, BL1-BL4, FR, and FL provided in the trunk area dimension measurement unit 200 and the platform unit 220.

Next, a method for measuring the trunk area width and the trunk area depth using the trunk area dimension measurement unit provided in the body fat measurement device according to the present embodiment will be described with reference to FIGS. 20 through 22.

FIGS. 20 through 22 are diagrams illustrating, in stages, a state in which the mobile portions 202a and 202b are moved forward (in the drawings, the direction of an arrow X2) in order to measure the trunk area dimensions. Here, FIG. 20 illustrates a state in which the mobile portions 202a and 202b are in the default positions; FIG. 21 illustrates a state in which the range sensors SA1 and SA2 are opposed to the left and right ends of the trunk area 301 of the measurement subject 300 as a result of the mobile portions 202a and 202b being pushed outward; and FIG. 22 illustrates a state in which the mobile portions 202a and 202b have been pushed further forward and have reached a position in which the mobile portions 202a and 202b cannot move any further.

The trunk area width is calculated from the outputs of the range sensors SA1 and SA2, outputted while the mobile portions 202a and 202b are moving. As shown in FIGS. 20 through 22, when the range sensors SA1 and SA2 are positioned to the left and right of the trunk area 301 of the measurement subject 300, the light emitted from the range sensors SA1 and SA2 is emitted toward the right side surface and the left side surface of the trunk area 301 of the measurement subject 300, respectively. Accordingly, the outputs from the range sensors SA1 and SA2 outputted while the mobile portions 202a and 202b are moving are outputs based on the respective distances from the range sensors SA1 and SA2 to the trunk area 301 of the measurement subject 300 in the horizontal direction.

Accordingly, in the same manner as in the aforementioned first embodiment of the present invention, the distances A1 and A2 between the range sensors SA1 and SA2 and the trunk area 301 of the measurement subject 300 when the range sensors SA1 and SA2 are opposed to the left and right ends of the trunk area 301 of the measurement subject 300 as shown in FIG. 21 are measured by detecting the minimum values of the outputs of the range sensors SA1 and SA2 while the mobile portions 202a and 202b are moving, and the trunk area width 2×a of the measurement subject 300 is calculated based on the aforementioned Formula (7) using the distances A1 and A2 and the predetermined distance A (that is, the distance between the range sensor SA1 and the range sensor SA2).

On the other hand, the trunk area depth is calculated from the output of the range sensor SB, which is provided on the display unit portion 230 in a fixed state. In other words, if the position of the trunk area dimension measurement unit 200 is adjusted so that the trunk area dimension measurement unit 200 is at a height corresponding to the location of the navel and so that the body axis is located in the center of the trunk area dimension measurement unit 200, and the location in which the range sensor SB is disposed is set so that the range sensor SB is disposed before the front end of the trunk area 301 of the measurement subject 300, the trunk area depth 2×b of the measurement subject 300 is calculated based on the aforementioned Formula (10) using the distance B3, which is a distance based on the output of the range sensor SB, and the predetermined distance B (the distance between the range sensor SB and the center of the electrode support member 216), as shown in FIG. 20.

In this manner, the body fat measurement device 1B according to the present embodiment is configured so that the trunk area width and the trunk area depth can be measured by the three range sensors SA1, SA2, and SB provided in the trunk area dimension measurement unit 200. To be more specific, in the body fat measurement device 1B according to the present embodiment, the mobile portions 202a and 202b are attached to the base portion 201 so that the mobile portions 202a and 202b can move along the trunk area depth direction, the trunk area width detection unit 24A is configured of the stated two range sensors SA1 and SA2 provided in predetermined positions on the mobile portions 202a and 202b, and the trunk area depth detection unit 24B is configured of the stated range sensor SB provided in a predetermined position on the base portion 201; as a result, the trunk area width and the trunk area depth can be measured.

Accordingly, by employing such a configuration, the trunk area width and trunk area depth can be measured with certainty and accurately without using many sensors; as a result, it is possible to realize a body fat measurement device that is capable of accurately measuring body fat masses such as visceral fat mass and that is easy to operate and use when taking such measurements, and that can be manufactured for a low cost. Moreover, by employing the aforementioned configuration, it is possible for the measurement subject to take measurements by him/herself without help from an assistant or the like, which makes it possible to realize a body fat measurement device that is suited to taking daily measurements of visceral fat masses or the like.

Furthermore, in the body fat measurement device 1B according to the present embodiment, the biasing force of the elastic members 203 for returning the mobile portions 202a and 202b provided in the trunk area dimension measurement unit 200 to their default positions is also used as a force (in FIGS. 21 and 22, a force F) for pressing the back area electrodes BU1-BU4 and BL1-BL4 against the back area surface of the trunk area 301 of the measurement subject 300 when the mobile portions 202a and 202b are being pushed forward; as a result, the back area electrodes BU1-BU4 and BL1-BL4 can be brought into contact with the back area surface of the trunk area 301 of the measurement subject 300 at a more appropriate compressive force and an in a stable manner. Therefore, employing the stated configuration makes a stable body fat mass measurement possible.

Note that in the first and second embodiments of the present invention, and the variations thereon, described thus far, it is preferable for the control unit 10 control the various functional blocks so that the measurement of the body impedance using the body impedance measurement unit 12 is started after the trunk area width and the trunk area depth have been detected by the trunk area width detection unit 24A and the trunk area depth detection unit 24B. By employing such a configuration, the body impedance measurement can be carried out after the trunk area dimensions have been actually measured, which makes it possible to prevent the occurrence of errors in the body fat mass measurement resulting from erroneous measurements of the trunk area dimensions.

Although the first and second embodiments of the present invention and the variations thereof described thus far provide examples of body fat measurement devices configured to be capable of taking actual measurements of both the trunk area width and the trunk area depth, in the case where another measurement means is provided and an actual measurement of the circumferential length of the trunk area (waist length) can be taken, the case where the device is configured so that the circumferential length of the trunk area is inputted as the measurement subject information, and so on, the device may be configured so that an actual measurement is taken of only one of the trunk area width and the trunk area depth, the other of the trunk area width and the trunk area depth is calculated based on the circumferential length of the trunk area, and a body fat mass is calculated based thereon.

In addition, in the aforementioned second embodiment of the present invention, the configuration includes the platform unit, and thus the platform unit may be provided with a body weight measurement function. In other words, the configuration may be such that a load cell or the like that serves as a body weight measurement unit for detecting a load on the platform unit is provided, which enables the weight of the measurement subject standing on the platform unit to be measured by the body weight measurement unit. In this case, if the configuration is such that body weight information measured by the body weight measurement unit provided in the platform unit is inputted into the control unit, the actual measured body weight of the target subject can be used as measurement subject information in the various types of computation processes.

In addition, although the aforementioned first and second embodiments of the present invention and the variations thereon describe examples in which the computation processing unit is configured so as to calculate the visceral fat cross-sectional area as the visceral fat mass and the subcutaneous fat cross-sectional area as the subcutaneous fat mass, the computation processing unit may be configured so that a different indicator than the visceral fat cross-sectional area, such as the visceral fat volume, visceral fat weight, visceral fat level, or the like is calculated as the visceral fat mass, and a different indicator than the subcutaneous fat cross-sectional area, such as the subcutaneous fat volume, subcutaneous fat weight, subcutaneous fat level, or the like is calculated as the subcutaneous fat mass.

In addition, although the aforementioned first and second embodiments of the present invention and the variations thereon describe examples in which the configuration is such that both the visceral fat cross-sectional area and the subcutaneous fat cross-sectional area are calculated and displayed, the configuration may be such that only one of these indicators is displayed, or that only the subcutaneous fat cross-sectional area is calculated and displayed. Furthermore, the configuration may be such that various types of body composition information aside from the visceral fat cross-sectional area and the subcutaneous fat cross-sectional area (for example, the body fat mass, area-by-area fat mass, fat-free mass, and so on) are calculated and displayed.

Furthermore, it is of course possible to combine the characteristic configurations in the aforementioned first and second embodiments of the present invention and the variations thereon without departing from the intended scope of the invention.

In this manner, the embodiments disclosed herein are to be understood in all ways as exemplary and in no ways limiting. The technical scope of the present invention is defined by the appended claims, and all variations that fall within the meaning and range of equivalency of the claims are intended to be embraced therein.

REFERENCE SIGNS LIST 1A, 1B body fat measurement device
10 control unit
11 computation processing unit
12 body impedance measurement unit
13 body shape information measurement unit
14 body composition information obtainment unit
14a visceral fat mass calculation unit
14b subcutaneous fat mass calculation unit
21 constant current generation unit
22 terminal switching unit
23 potential difference detection unit
24A trunk area width detection unit
24B trunk area depth detection unit
25 measurement subject information input unit
26 display unit
27 operating unit
27a measure button
28 power source unit
29 memory unit
100A-100E trunk area dimension measurement unit
101 base portion
102, 102a-102c mobile portion
103 elastic member
110 frame member
111 upper frame portion
112 right-side frame portion
112a leg portion
113 left-side frame portion
113a leg portion
120 back area electrode support unit
121 mat
122A right arm fitting unit
122B left arm fitting unit
123A right leg fitting unit
123B left leg fitting unit
130 main body unit
132 connection cable
200 trunk area dimension measurement unit
201 base portion
202a, 202b mobile portion
203 elastic member
210 frame member
211 rear frame portion
212 right-side frame portion
213 left-side frame portion
214 front frame portion
215 connection portion
216 electrode support member
220 platform unit
221 platform portion
230 display unit portion
232 connection cable
300 measurement subject
301 trunk area
302A right arm
302B left arm
303A right leg
303B left leg
400 bed surface
HR, HL arm electrode
BU1-BU4, BL1-BL4 back area electrode
FR, FL leg electrode
SA1, SA2, SB range sensor

The invention claimed is:

1. A body fat measurement device comprising:
a plurality of electrodes for making contact with predetermined areas of the surface of a measurement subject's body;
a body impedance measurement unit that measures a body impedance of the measurement subject's body using said plurality of electrodes;
a trunk area dimension detection unit for detecting a trunk area dimension of the measurement subject;
a frame-shaped trunk area dimension measurement unit in which said trunk area dimension detection unit is provided and that is capable of being disposed so as to surround the measurement subject's trunk area;
a body shape information measurement unit that measures a dimension of the measurement subject's trunk area based on information detected by said trunk area dimension detection unit; and
a body fat mass calculation unit that calculates a body fat mass based on the body impedance measured by said body impedance measurement unit and the trunk area dimension measured by said body shape information measurement unit,
wherein said trunk area dimension measurement unit includes a base portion whose position relative to the measurement subject's trunk area does not change in a state where the trunk area dimension measurement unit is disposed surrounding the measurement subject's trunk area, and a mobile portion that is attached in a movable state to said base portion and whose position relative to the measurement subject's trunk area can change along a first direction that is one of a trunk area width direction and a trunk area depth direction of the measurement subject in a state where the trunk area dimension measurement unit is disposed surrounding the measurement subject's trunk area;
said trunk area dimension detection unit includes a non-contact range sensor that is provided on the surface of said mobile portion in an area that configures a surface on an inner side of said trunk area dimension measurement unit and that detects a distance between said mobile portion and an object opposed thereto in a second direction that is the other of the trunk area width direction and the trunk area depth direction of the measurement subject, and a movement amount detection sensor that detects an amount by which said mobile portion moves along said first direction;
said body shape information measurement unit measures a trunk area width and a trunk area depth of the measurement subject based on distance information detected by said range sensor while said mobile portion is moving and movement amount information detected by said movement amount detection sensor;
with respect to measurement of the trunk area dimension that, of the trunk area width and trunk area depth of the measurement subject, matches said second direction, said body shape information measurement unit calculates that dimension using only said distance information; and
with respect to measurement of the trunk area dimension that, of the trunk area width and trunk area depth of the measurement subject, matches said first direction, said body shape information measurement unit associates said distance information with said movement amount information and calculates that dimension using said movement amount information that corresponds to characteristic points appearing in said distance information.

2. The body fat measurement device according to claim 1, further comprising:
a biasing member that biases said mobile portion toward one side of said first direction, which is the direction in which said mobile portion moves.

3. The body fat measurement device according to claim 1, further comprising:
a control unit that controls the operations of said body impedance measurement unit, said trunk area dimension detection unit, said body shape information measurement unit, and said body fat mass calculation unit,
wherein said control unit carries out control for driving said body impedance measurement unit to start measuring the body impedance after the trunk area dimension has been measured by said body shape information measurement unit unit.

4. The body fat measurement device according to claim 1, wherein said plurality of electrodes includes trunk area electrodes for making contact with the surface of the measurement subject's trunk area;
said trunk area electrodes are disposed below the measurement subject's trunk area when the measurement subject is lying down; and
said trunk area dimension measurement unit is disposed so as to surround the measurement subject's trunk area when the measurement subject is lying down.

5. The body fat measurement device according to claim 1, wherein said plurality of electrodes includes trunk area electrodes for making contact with the surface of the measurement subject's trunk area; and
said trunk area electrodes are provided on said base portion of said trunk area dimension measurement unit.

6. The body fat measurement device according to claim 1, wherein said plurality of electrodes includes back area electrodes for making contact with the surface of a back area that corresponds to an area of the measurement subject's trunk area on the back side thereof.

7. The body fat measurement device according to claim 1, wherein the body fat mass calculation unit includes at least one of a visceral fat mass calculation unit thatcalculates the visceral fat mass of the measurement subject and a subcutaneous fat mass calculation unit calculates the subcutaneous fat mass of the measurement subject.

* * * * *